United States Patent [19]

Shimizu et al.

[11] Patent Number: 5,260,477
[45] Date of Patent: Nov. 9, 1993

[54] METHOD FOR PREPARING ALPHA-(4-ISOBUTYLPHENYL)PROPIONIC ACID OR ITS PRECURSOR

[75] Inventors: Isoo Shimizu; Yasuo Matsumura; Yuichi Tokumoto; Kazumichi Uchida, all of Yokohama, Japan

[73] Assignee: Nippon Petrochemicals Co., Ltd., Tokyo, Japan

[21] Appl. No.: 452,804

[22] Filed: Dec. 18, 1989

[30] Foreign Application Priority Data

Dec. 21, 1988 [JP] Japan .................. 63-323143
Dec. 21, 1988 [JP] Japan .................. 63-323144

[51] Int. Cl.⁵ ............................. C07C 69/76
[52] U.S. Cl. ........................ 560/105; 562/406; 568/428; 568/429; 568/814
[58] Field of Search ............... 562/406; 560/105; 568/428, 429, 814

[56] References Cited

U.S. PATENT DOCUMENTS

| | | | |
|---|---|---|---|
| 3,959,364 | 5/1976 | Armitage et al. | 560/105 |
| 3,965,161 | 6/1976 | Kogure et al. | 560/105 |
| 4,143,229 | 3/1979 | Sabbatini | 560/496 |
| 4,329,507 | 5/1982 | Takeda et al. | 568/332 |
| 4,350,825 | 9/1982 | Huang | 562/406 |
| 4,694,100 | 9/1987 | Shimizu et al. | 560/105 |
| 4,937,362 | 6/1990 | Tonaka | 562/406 |

FOREIGN PATENT DOCUMENTS

| | | |
|---|---|---|
| 170147 | 2/1986 | European Pat. Off. |
| 1549758 | 12/1968 | France |
| 59-10545 | 7/1982 | Japan |
| 971700 | 9/1964 | United Kingdom |
| 1160725 | 8/1969 | United Kingdom |
| 1549140 | 7/1979 | United Kingdom |

*Primary Examiner*—Paul J. Killos
*Attorney, Agent, or Firm*—Scully, Scott, Murphy & Presser

[57] ABSTRACT

A method for preparing α-(4-isobutylphenyl)propionic acid or its precursor is here disclosed which comprises a step (I) of dehydrogenating p-isobutylethylbenzene in a gaseous phase in the presence of a dehydrogenating metal catalyst to form p-isobutylstyrene and at least one unsaturated hydrocarbon compound selected from a group A defined in Claim 1; a step (II) of reacting p-isobutylstyrene obtained in the step (I) with carbon monoxide and hydrogen or with carbon monoxide and water or a lower alcohol in the presence of a transition metal complex carbonylating catalyst to form α-(4-isobutylphenyl)propionic acid or its precursor; and a step (III) of hydrogenating at least one unsaturated hydrocarbon compound selected from the group A obtained in the dehydrogenation step (I) to form p-isobutylethylbenzene, and recycling the thus formed p-isobutylethylbenzene through the step (I) as the raw material of the step (I).

25 Claims, 1 Drawing Sheet

METHOD FOR PREPARING ALPHA-(4-ISOBUTYLPHENYL)PROPIONIC ACID OR ITS PRECURSOR

BACKGROUND OF THE INVENTION (i) Field of the Invention

The present invention is a method for preparing α-(4-isobutylphenyl)propionic acid or its precursor, i.e., an alkyl α-(4-isobutylphenyl)propionate, α-(4-isobutylphenyl)propionaldehyde or 2-(4-isobutylphenyl)propanol economically and in a high purity.

More specifically, the present invention relates to an ecomonical method for preparing α-(4-isobutylphenyl)propionic acid or its precursor which comprises a dehydrogenation step of dehydrogenating p-isobutylethylbenzene in a gaseous phase in the presence of a dehydrogenating metal catalyst to form olefins including p-isobutylstyrene and the like as by-products; a carbonylation step of reacting the formed p-isobutylstyrene with carbon monoxide and water or an alcohol in the presence of a transition metal complex carbonylating catalyst to form α-(4-isobutylphenyl)propionic acid or its precursor; and a hydrogenation step of hydrogenating the formed olefin by-products to convert the same into p-isobutylethylbenzene and hydrogenating the other by-products formed in the carbonylation step to form α-(4-isobutylphenyl)propionic acid or its precursor.

This α-(4-isobutylphenyl)propionic acid is a useful medicine (trade name Ibuprophen) having alleviation effects of fever and pain and antiphlogistic effect, as described in British Patent No. 971700 and French Patent No. 1549758.

On the other hand, it is known that the alkyl α-(4-isobutylphenyl)propionate can be easily converted into α-(4-isobutylphenyl)propionic acid by hydrolysis with an acid or an alkali in a known manner. Similarly, it is also known that α-(4-isobutylphenyl)propionaldehyde and α-(4-isobutylphenyl)propanol can be easily converted into α-(4- ) isobutylphenyl)propionic acid by oxidation in a known manner. Therefore, these compounds can all be considered to be the precursors of α-(4-isobutylphenyl)propionic acid.

(ii) Description of the Prior Art

Heretofore, α-(4-isobutylphenyl)propionic acid and its precursor have been synthesized from an extremely great number of compounds as starting materials by various methods.

However, in order to synthesize α-(4-isobutylphenyl)propionic acid and its precursor at a low cost and in a high purity, the following requirements are needful:

(a) Starting materials should be simple compounds.

(b) In a reaction to be utilized, an intermediate in each step should also be as simple and stable as possible.

(c) In place of expensive reagents, inexpensive reagents or catalysts should be employed.

(d) It is necessary that by-products can be effectively utilized.

(e) The number of steps for the synthesis should be as few as possible.

(f) Since an isobutyl group is liable to bring about isomerization, it is necessary to use a reaction in which the isomerization and other undesirable phenomenons are inhibited as much as possible.

For example, in Japanese Patent Laid-open Publication No. 52-65243 and U.S. Pat. No. 3959364 which suggest synthetic methods of α-(4-isobutylphenyl)propionic acid or its alkyl esters, complicate and expensive compounds or Grignard reagents which are unstable and difficult to handle are utilized as starting materials themselves. Therefore, these suggested methods are not always considered to be economical from an industrial viewpoint.

Additionally, in all of Japanese Patent Laid-open Publication No. 50-4040 which disclose methods for the preparation of α-(4-isobutylphenyl)propionic acid, isobutylbenzene is used as the starting material, but aluminum chloride is used as a catalyst, and thus, an isobutyl group tends to isomerize. In addition, expensive reagents are used.

In methods described in French Patent No. 1549758, British Patent Nos. 1160725 and 1549140, U.S. Pat. Nos. 3965161 and 4143229, Japanese Patent Laid-open Publication Nos. 52-57338, 52-97930, 53-18535 and 56-154428, p-isobutylacetophenone is used as the starting material.

However, p-isobutylacetophenone is not considered to be an inexpensive compound for the undermentioned reason. The most economical synthesis of p-isobutylacetophenone is to use isobutylbenzene as the starting material, but it is not preferable from an economical viewpoint to convert isobutylbenzene into p-isobutylacetophenone. That is, for the sake of the conversion into p-isobutylacetophenone, it is indispensable to make use of acetyl chloride which is an expensive and unstable material, and in addition, anhydrous aluminum chloride which is very sensitive to water must be used as a reaction catalyst at least in an amount equimolar with acetyl chloride, i.e., in a large amount. For example, even if this conversion reaction proceeds stoichiometrically in a yield of 100%, anhydrous aluminum chloride as much as 700 kg must be used to manufacture 1 ton of p-isobutylacetophenone. Moreover, after the end of the reaction, 410 kg of aluminum hydroxide and 750 kg of a chlorine ion result from the inactivation of anhydrous aluminum chloride, and thus it is additionally necessary to treat 1,160 kg of wastes, the amount of which is much greater than that of the manufactured p-isobutylacetophenone, so as to make them harmless. For this reason, needless to say, p-isobutylacetophenone itself as the starting material is expensive. Furthermore, the conversion of p-isobutylacetophenone into α-(4-isobutylphenyl)propionic acid or its alkyl esters proceeds via intricate intermediates, and it is fair to say that the known method is not always economical from an industrial viewpoint.

Japanese Patent Laid-open Publication Nos. 52-97930 and 59-10545 and US Patent No. 4329507 suggest methods for preparing α-(4-isobutylphenyl)propionic acid from p-isobutylstyrene through a hydroformylation reaction or a Reppe reaction. These methods using p-isobutylstyrene are economically excellent as techniques for preparing α-(4-isobutylphenyl)propionic acid, because p-isobutylstyrene which is the starting material is simple and stable, and because the hydroformylation reaction and the Reppe reaction do not require expensive reagents. However, in these conventional manufacturing methods of p-isobutylstyrene, a complex reaction route is taken or expensive reagents are employed, so that the above-mentioned advantages are lost.

U.S. Pat. No. 4694100 discloses a method which comprises subjecting isobutylbenzene and acetaldehyde to condensation reaction in the presence of a sulfuric acid catalyst to form 1,1-bis(p-isobutylphenyl)ethane, catalystically decomposing the latter to p-isobutylstyrene by the use of an acid catalyst, reacting the resultant compound with carbon monoxide and water or with carbon monoxide and an alcohol in the present of a carbonylation complex catalyst in order to obtain α-(4-isobutylphenyl)propionic acid or its alkyl ester. However, since the above-mentioned method employs sulfuric acid, the sulfonation reaction of isobutylbenzene itself which is the valuable raw material for the manufacture of 1,1-bis(p-isobutylphenyl)ethane cannot be avoided, so that a part of isobutylbenzene is lost as a sulfonated compound, which means that the method is economically unpreferable. In addition, since this condensation reaction is a dehydration reaction, sulfuric acid which is used as the catalyst is diluted with the resulting water, and thus in order to reuse the catalyst, the diluted sulfuric acid must be treated by, for example, high-temperature distillation, in which devices are inconveniently liable to corrode. Additionally, a great deal of the sulfonated compound is dissolved in a sulfonic acid phase, and therefore the catalyst concentration cannot be easily recovered by the simple distillation. In consequence, the resultant water must be removed through chemical reaction by the use of anhydrous sulfuric acid or fuming sulfuric acid, with the result that the cost of the catalyst increases.

As discussed above, the conventional techniques regarding the manufacture of α-(4-isobutylphenyl)propionaldehyde or its alkyl ester are not considered yet to be economical.

As already described, p-isobutylstyrene is a useful intermediate in manufacturing α-(4-isobutylphenyl)propionic acid, and if this p-isobutylstyrene is utilized, α-(4-isobutylphenyl)propionic acid can be prepared inexpensively and easily. Accordingly, a novel method for this p-isobutylstyrene is desired.

By way of one technique of manufacturing p-isobutylstyrene at a low cost, the dehydrogenation of p-isobutylethylbenzene can be considered.

However, in the product by subjecting p-isobutylethylbenzene to the dehydrogenation reaction, olefin by-products are inevitably present to some extent together with p-isobutylstyrene. In addition, inventors of the present application have found the following fact through experiments: Some compounds of the above-mentioned olefin by-products are sensitive to hydroformylation, hydrocarboxylation or hydroesterification, and therefore they trigger troubles in the carbonylation of p-isobutylstyrene. In view of the object of the present invention that a medicine or its precursor is prepared, necessary means must be taken so as to eliminate the unpreferable functions of these olefin by-products in the carbonylation step.

SUMMARY OF THE INVENTION

The present invention is directed to a technique for preparing α-(4-isobutylphenyl)propionic acid or its precursor at a low cost and in a high purity by effectively utilizing both of olefin by-products obtained in the dehydrogenation of p-isobutylethylbenzene and by-products obtained in the carbonylation of these compounds.

A first feature of the present invention is connected for preparing α-(4-isobutylphenyl)propionic acid or its precursor which comprises the following steps (I), (II) and (III):

the step (I) of dehydrogenating p-isobutylethylbenzene in a gaseous phase in the presence of a dehydrogenating metal catalyst to form p-isobutylstyrene and any unsaturated hydrocarbon compound selected from the group A;

the group A:
4-(2'-methyl-1'-propenyl)ethylbenzene,
4-(2'-methyl-1'-propenyl)vinylbenzene,
4-(2'-methyl-2'-propenyl)ethylbenzene, and
4-(2'-methyl-2'-propenyl)vinylbenzene;

the step (II) of reacting p-isobutylstyrene obtained in the step (I) with carbon monoxide and hydrogen or with carbon monoxide and water or a lower alcohol in the presence of a transition metal complex carbonylating catalyst to form α-(4-isobutylphenyl)propionic acid or a precursor of α-(4-isobutylphenyl)propionic acid which is an alkyl α-(4-isobutylphenyl)propionate or α-(4-isobutylphenyl)propionaldehyde; and the step (III) of hydrogenating at least one selected from the unsaturated hydrocarbon compounds in the group A obtained in the previous dehydrogenation step (I) to form p-isobutylethylbenzene, and recycling the thus formed p-isobutylethylbenzene through the previous step (I) as the raw material in the previous step (I), if necessary.

DETAILED DESCRIPTION OF THE INVENTION

Figure 1:
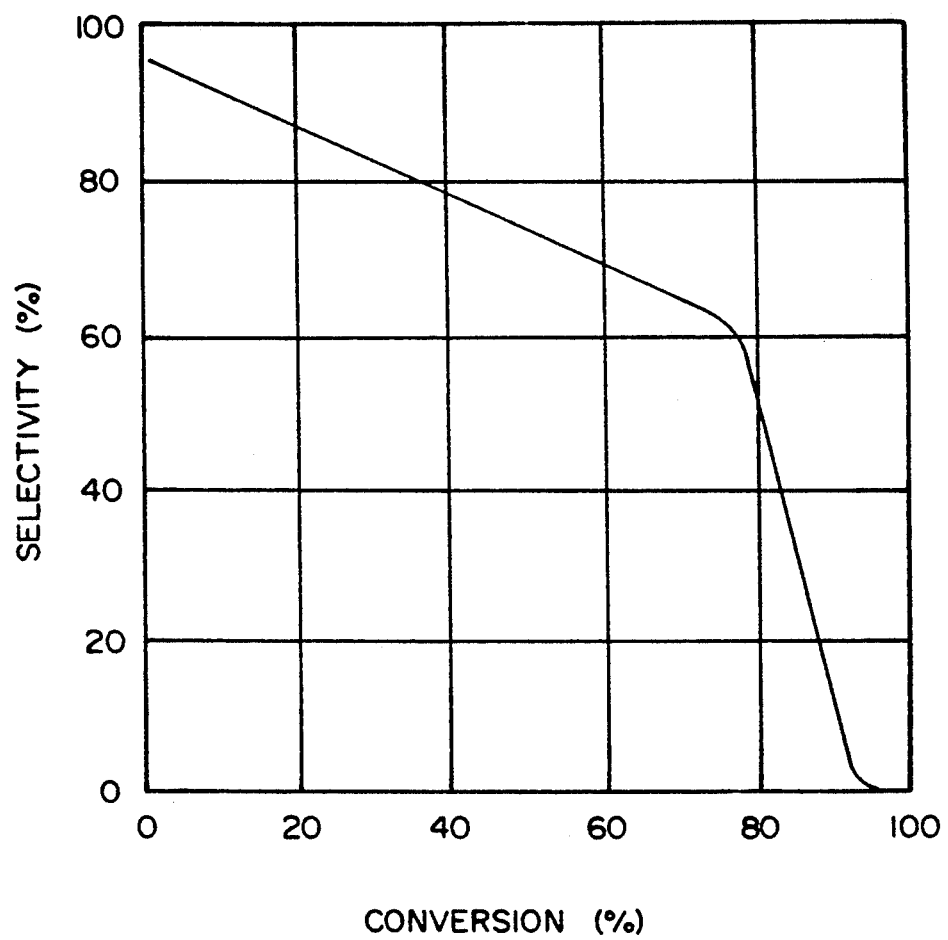
FIG. 1 shows a relation between the conversion of p-isobutylethylbenzene and the selectivity of of p-isobutylstyrene in dehydrogenation reaction of the present invention. In this drawing, solid lines indicate results of Experimental Examples 1 to 10 of the present invention.

The present invention will be described in detail together with the other features of the present case.

Dehydrogenation Step

In the dehydrogenation step (I) in the method of the present invention, p-isobutylethylbenzene is dehydrogenated in the presence of a dehydrogenating metal catalyst to form p-isobutylstyrene. More specifically, this dehydrogenation step intends to prepare p-isobutylstyrene by selectively dehydrogenating an ethyl group alone of p-isobutylethylbenzene.

As p-isobutylethylbenzene which is the raw material in the dehydrogenation step (I), what has been prepared by an optional manufacturing process can be used. For example, p-isobutylethylbenzene can be used which has been manufactured by reacting isobutylbenzene with ethylene in the presence of an acid catalyst.

The dehydrogenation catalyst is a metallic catalyst containing a metal selected from the groups IB, IIB, VIA, VIIA and VIII of the periodic table. Typical examples of the catalyst include metallic compounds of iron, copper, zinc, nickel, palladium, platinum, cobalt, rhodium, iridium, ruthenium, chromium and molybdenum, and combinations of these compounds may be also used effectively. These metals can be used in the form of a simple substance or in the form of an oxide, a chloride, a sulfide or a hydrogen-treated compound. The preferable catalyst contains at least one metal selected from iron, copper and chromium. In particular, the iron oxide catalyst and the copper-chromium catalyst containing copper oxide and chromium oxide are effective in the dehydrogenation step (I) of the present invention, since they have the high selectivity of p-isobutylstyrene.

Usually, the hydrogenation catalyst loses its activity gradually owing to coking and the like, while used for a long period of time. When lost, the initial activity of the catalyst can be recovered by decoking at a high temperature of, e.g., 500° C. or so with air or the like. Alternatively, the activity can be also recovered, if necessary, by putting the catalyst in a hydrogen flow at a temperature of 200 to 500° C. so as to perform a hydrogen treatment.

The reaction temperature of the dehydrogenation depends upon the composition of the catalyst, the contact time and the grade of the dilution, but it is usually from 300 to 650° C., preferably 400° to 650° C. When the reaction temperature is more than this range, secondary reactions such as decomposition reactions and the further dehydrogenation of formed p-isobutylstyrene occur vigorously, so that the selectivity coefficiently of p-isobutylstyrene deteriorates noticeably. In consequence, a great deal of p-isobutylethylbenzene is lost, and the distribution of the products is complicated fairly, with the result that it is difficult to separate p-isobutylstyrene and p-isobutylethylbenzene by the distillation or the like. When the reaction temperature is less than the above-mentioned range, a reaction rate lowers perceptibly, which is not economical, though the selectivity coefficient of p-isobutylbenzene is high.

Olefins formed by the dehydrogenation reaction are polymerizable, and thus if they are kept up at a high temperature in a high concentration in a reaction layer, a part of produced p-isobutylstyrene is polymerized and lost. In order to effectively avoid this undesirable phenomenon, it is effective that the concentration of olefins is diluted with a non-reducing gas such as a nitrogen gas, a helium gas, an argon gas, steam or an oxygen gas. In addition, the olefins may be diluted with a solvent such as benzene which is hardly dehydrogenated. Furthermore, in order to maintain the catalyst activity for the dehydrogenation, steam can be fed to the reaction layer in the course of the dehydrogenation. In this case, the amount of steam is not particularly limited.

A reaction system in the dehydrogenation step (I) may be any of a fixed bed, a moving bed and a fluidized bed.

The reaction pressure for the dehydrogenation is not particularly limited, so long as it permits vaporizing p-isobutylstyrene produced under the above-mentioned reaction conditions. Nevertheless, the reaction pressure is usually 50 kg/cm$^2$ or less, and a level of from atmospheric pressure to 10 kg/cm$^2$ is preferable and economical.

The time of contact with the raw material p-isobutylethylbenzene is in the range of 0.005 to 20 seconds, preferably 0.01 to 10 seconds, more preferably 0.05 to 5 seconds. When the contact time is less than the above-mentioned range, reaction efficiency is inconveniently low. When it is more than the above-mentioned range, produced p-isobutylstyrene is further secondarily dehydrogenated, and the selectivity coefficient of p-isobutylstyrene lowers unpreferably. The contact time can be suitably altered in the above-mentioned range in accordance with a combination of the selected reaction system, the composition of a reaction gas, the composition of a catalyst, the reaction temperature, the preheating temperature of the raw material gas and the like.

Needless to say, the dehydrogenation step (I) can be carried out by a continuous system or a batch system.

The researches of the present inventors have elucidated that in the present invention, the influence of the reaction conditions and factors on the reaction can be represented by the conversion of p-isobutylethylbenzene and the selectivity coefficient of p-isobutylstyrene.

That is, the relation between the optional conversion x of p-isobutylethylbenzene obtained under the above-mentioned reaction conditions and the selectivity coefficient y of p-isobutylstyrene can be represented by the linear function $$y = ax + b$$

wherein a and b are inherent constants of the catalyst.

FIG. 1 shows the relation between the conversion of p-isobutylethylbenzene and the selectivity coefficient of p-isobutylstyrene obtained in the undermentioned examples (hereinafter referred to as "dehydrogenation performance straight line"). For example, if certain factors of the reaction conditions are set, a point on the dehydrogenation performance straight line corresponding to a certain conversion indicates the selectivity coefficient of p-isobutylstyrene which can be actually obtained. Therefore, the reaction conditions can be chosen so as to obtain the conversion of p-isobutylethylbenzene corresponding to the desired selectivity coefficient in accordance with the dehydrogenation performance straight line of the used dehydrogenation catalyst. For example, in the case of the copper-chromium catalyst, it is suitable in the present invention that the conversion of p-isobutylethylbenzene is maintained at 80% by weight or less, preferably 60% by weight or less, more preferably 50% by weight. Furthermore, in the case of the iron oxide catalyst, it is suitable in the present invention that the conversion of p-isobutylethylbenzene is maintained preferably at 80% by weight or less, more preferably 70% by weight or less. If the conversion is in excess of the range, the selectivity coefficient of p-isobutylstyrene deteriorates rapidly and diverges from the dehydrogenation performance straight line, so that not only by-products but also cracked products increase unpreferably. In the case that the conversion is in the above-mentioned range, the lower the conversion is, the higher the selectivity coefficient is. However, the productivity of p-isobutylstyrene is the product of the conversion and the selectivity coefficient, and therefore the employment of the low conversion is unpreferable, because the separation and recovery operation of unreacted p-isobutylethylbenzene by the subsequent distillation is very burdensome. From an economical viewpoint, it is desirable that the conversion is maintained at a level of 5% by weight or more.

As discussed above, if p-isobutylethylbenzene is dehydrogenated in the dehydrogenation step of the present invention, the ethyl group is exclusively dehydrogenated against conventional expectation, so that it becomes possible to prepare p-isobutylstyrene in the surprisingly high selectivity coefficient.

However, by the above-mentioned dehydrogenation step that the olefin by-product mentioned below is formed to some extent depending on the reaction condition. In this dehydrogenation step (I), the olefin by-product is any of the olefins in the following group A:

the group A:
4-(2'-methyl-1'-propenyl)ethylbenzene,
4-(2'-methyl-1'-propenyl)vinylbenzene,
4-(2'-methyl-2'-propenyl)ethylbenzene, and 4-(2'-methyl-2'-propenyl)vinylbenzene;

Hydrogenation

Any olefin by-product can be converted into the raw material isobutylethylbenzene by hydrogenating the byproduct itself.

Therefore, after the dehydrogenation step, p-isobutylstyrene is separated and recovered by distillation, and the by-product which is the remaining unsaturated hydrocarbon compound in the group A is hydrogenated in a usual manner, so that the carbon-carbon double bond in a substituted propenyl group or a vinyl group of the by-product compound is hydrogenated to form p-isobutylethylbenzene.

A part or all of the thus formed p-isobutylethylbenzene can be recycled as the raw material in the above-mentioned dehydrogenation step (I). In this way, the olefin by-product of the dehydrogenation step can be utilized effectively.

In the hydrogenation step, any expensive hydrogenating agent is not necessary, and the preferable hydrogenation can be achieved by reacting the olefin by-product with hydrogen in the presence of a conventional known hydrogenating metallic catalyst.

The hydrogenating catalyst in the hydrogenation step can be suitably selected from the conventional known hydrogenating metallic catalysts which hydrogenate the ethylenic carbon-carbon unsaturated double bond but do not hydrogenate the nucleus of an aromatic ring. Typical examples of these catalysts include metallic catalysts containing metals such as Fe, Co, Ni, Ru, Rh, Pd, Os, Ir, Pt, Cu, Re, Mo, W, Cr and Ta. These metallic catalysts, when used, can be supported on a suitable carrier such as silica, silica-alumina, pumice stone or carbon. A reaction product depends upon the kind of catalyst, conditions of the hydrogenation reaction and the like, but the reaction product can be selected taking an activity of the catalyst into consideration on condition that the ethylenic carbon-carbon double bond is hydrogenated but the nucleus of the aromatic ring is not hydrogenated.

In general, the reaction temperature of the hydrogenation is from ordinary temperature to 300° C., and a hydrogen pressure is from atmospheric pressure to 300 kg/cm$^2$.

A solvent for the hydrogenation of the present invention can be used without any limitation, so long as it does not impede the purpose of this step.

Carbonylation

In the step (II) of the present invention, p-isobutylstyrene obtained in the dehydrogenation step (I) is carbonylated to form α-(4-isobutylphenyl)-propionic acid or its precursor. As techniques of this carbonylation, there are hydroformylation regarding a reaction with carbon monoxide and hydrogen to produce an aldehyde, hydrocarboxylation regarding a reaction with carbon monoxide and water to produce an acid, and hydroesterification regarding a reaction with carbon monoxide and a lower alcohol to produce an ester.

In the above-mentioned p-isobutylethylbenzene dehydrogenation step, p-isobutylstyrene is formed as the main component, but any of the four olefin by-products in the group A is also formed to some extent depending on the reaction condition. Needless to say, in the carbonylation step, it is preferable that the olefin by-product is not contained in p-isobutylstyrene, since if not, the reaction proceeds in a simple state.

Therefore, according to one procedure of the present invention, the olefin by-product is separated and removed by distillation or the like, and high-purity p-isobutylstyrene is then fed to the subsequent carbonylation step. This procedure is preferable, because when the thus separated olefin by-product is hydrogenated, p-isobutylethylbenzene is formed which can be recycled as the raw material in the dehydrogenation step.

However, the boiling point of the component to be separated is close to that of p-isobutylstyrene, and therefore the means, e.g., distillation for separating the olefin by-product from the dehydrogenated reaction product is not always effective.

Here, the present inventors have found that even if a mixture of p-isobutylstyrene and any of the above-mentioned four olefin by-products is carbonylated together, α-(4-isobutylphenyl)propionic acid or its precursor can be prepared at a low cost and in a high purity, whereby the object of the present invention can be achieved.

That is, p-isobutylstyrene obtained in the previous dehydrogenation step (I) can be fed to the subsequent carbonylation step in the form of a mixture containing at least one olefin by-product or if necessary, only through a simple distillation, without separating and removing the olefin by-product accurately.

Therefore the preferable material to be fed to the next step of the carbonylation step (II) in the present invention is a mixture comprising p-isobutylstyrene and at least one unsaturated hydrocarbon compound selected from the group consisting of 4-(2'-methyl-1'-propenyl)ethylbenzene and 4-(2'-methyl-2'-propenyl)ethylbenzene, a mixture comprising p-isobutylstyrene and at least one unsaturated hydrocarbon compound selected from the group consisting of 4-(2'-methyl-1'-propenyl)vinylbenzene and 4-(2'-methyl-2'-propenyl)vinylbenzene, or a mixture thereof.

Hydroformylation

In the first place, reference will be made to the hydroformylation reaction of the carbonylation step (II) in which p-isobutylstyrene is reacted with carbon monoxide and hydrogen.

In the hydroformylation step of the present invention, p-isobutylstyrene obtained in the above-mentioned dehydrogenation step (I) is converted into α-(4-isobutylphenyl)propionaldehyde by a hydroformylation using carbon monoxide and hydrogen in the presence of a transition metal complex catalyst.

It has also been found that specific carbonylation conditions function so as to surprisingly more inhibit the activity of a substituted propenyl group in 4-(2'-methyl-1'-propenyl)ethylbenzene, 4-(2'-methyl-1'-propenyl)vinylbenzene, 4-(2'-methyl-2'-propenyl)ethylbenzene or 4-(2'-methyl-2'-propenyl)vinylbenzene which is the olefin by-product in the group A than that of a vinyl group in the olefin by-product.

This fact will be further described in detail: The compounds 4-(2'-methyl-1'-propenyl)ethylbenzene and 4-(2'-methyl-2'-propenyl benzene of the four olefin by-products substantially scarcely react under the specific carbonylation conditions of the present invention. On the other hand, under the same carbonylation conditions, 4-(2'-methyl-1'-propenyl)vinylbenzene and 4-(2'-methyl-2'-propenyl)vinylbenzene are substantially hydroformylated only on the vinyl group thereof, but the substituted propenyl group substantially scarcely reacts.

That is, under the specific hydroformylation conditions of the present invention, 4-(2'-methyl-1'-propenyl)vinylbenzene is hydroformylated to α-[4-(2'-methyl-1'-propenyl)phenyl]propionaldehyde, and 4-(2'-methyl-2'-propenyl)vinylbenzene is hydroformylated to α-[4-(2'-methyl-2'-propenyl)phenyl]propionaldehyde.

In the case that the simple distillation has been made to separate the olefin by-product, the above-mentioned reaction results can be obtained similarly both when the olefin by-product is carbonylated singly and when the mixture of the four olefin by-products in which p-isobutylstyrene may be present is carbonylated. Needless to say, when p-isobutylstyrene is carbonylated in the form of the olefin mixture containing any of the olefin by-products, p-isobutylstyrene can be similarly converted into α-(4-isobutylphenyl)propionaldehyde efficiently in the hydroformylation step.

The transition metal complex carbonylation catalyst used in the hydroformylation contains a transition metal such as palladium, rhodium, iridium or ruthenium. The usable transition metal can have an oxidation number of from 0 to a maximum value, and the usable complex contains, as a ligand, a halogen atom, a trivalent phosphorus compound, a π-allyl group. an amine, a nitrile, an oxime, an olefin, carbon monoxide or hydrogen.

Typical examples of the catalyst include bistriphenylphosphinedichloro complex, bistributylphosphinedichloro complex, bistricyclohexylphosphinedichloro complex, π-allyltriphenylphosphinedichloro complex, triphenylphosphinepiperidinedichloro complex, bisbenzonitriledichloro complex, biscyclohexyloximedichloro complex, 1,5,9-cyclododecatrienedichloro complex, bistriphenylphosphinedicarbonyl complex, bistriphenylphosphine acetate complex, bistriphenylphosphine dinitrate complex, bistriphenylphosphine sulfate complex, tetrakistriphenylphosphine complex, chlorocarbonylbistriphenylphosphine complex having carbon monoxide as a part of a ligand, hydridocarbonyltristriphenylphosphine complex, bischlorotetracarbonyl complex and dicarbonylacetyl acetonate complex.

The catalyst can be used by feeding the same to a reaction system in the form of the complex, or alternatively, a compound which will be a ligand is separately fed to the reaction system, and the complex is formed therefrom in the system and then used as the carbonylating catalyst. That is, this procedure can be carried out by simultaneously adding, to the reaction system, an oxide, a sulfate or a chloride of the above-mentioned transition metal and a compound, which will be the ligand, such as a phosphine, a nitrile, an allyl compound, an amine, an oxime, an olefin, carbon monoxide or hydrogen.

Examples of the phosphine are triphenylphophine, tritolylphophine, tributylphosphine, tricyclohexylphosphine and triethylphosphine; examples of the nitrile include benzonitrile, acrylonitrile, propionitrile and benzylnitrile; examples of the allyl compound are allyl chloride and allyl alcohol; examples of the amine are benzylamine, pyridine, piperazine and tri-n-butylamine; and examples of the oxime are cyclohexyloxime, acetoxime, benzoaldoxime; and examples of the olefin are 1,5-cyclooctadiene and 1,5,9-cyclododecatriene.

The amount of the complex catalyst or the compound which is used to produce the complex is in the range of 0.0001 to 0.5 mol, preferably 0.001 to 0.1 mol per mol of an olefin such as p-isobutylstyrene. Furthermore, the amount of the compound which will be the ligand is in the range of 0.8 to 10 mols, preferably 1 to 4 mols per mol of a transition metal, which will be the nucleus of the complex, such as palladium, rhodium, iridium or ruthenium.

For the purpose of accelerating the reaction, it is possible to add an inorganic halide such as hydrogen chloride or boron trifuloride, or an organic iodide such as methyl iodide.

The amount of the halide to be added is in the range of 0.1 to 30-fold mols, preferably 1 to 15-fold mols as much as that of the complex catalyst or the compound used to form the complex. When the amount of the halide is less than 0.1 mol, the effect of the added halide cannot be perceived, depending upon the kind of catalyst. Inversely, when it is more than 30-fold mols, the activity of the catalyst declines unexpectedly, and the halogen is added to the double bond of p-isobutylstyrene, which inhibits the intended reaction.

The hydroformylating reaction is performed at a reaction temperature of 40° to 150° C., preferably 55° to 110° C. When the reaction temperature is less than 40° C., a reaction rate is too low to be practical; when it is more than 150° C., secondary reactions such as polymerization and hydrogenation as well as the decomposition of the complex catalyst tend to occur inconveniently.

Reaction pressure can be suitably selected, in so far as it is 10 kg/cm$^2$ or more. When the reaction pressure is less than 10 kg/cm$^2$, the reaction rate is too low to be practical. The higher the reaction pressure is, the higher the reaction rate is conveniently. However, when the pressure is too high, it is required to heighten pressure resistance of a reaction vessel, and therefore limitation is naturally present. In practice, the upper limit of the pressure is usually 600 kg/cm$^2$.

The reaction is performed until a mixed gas of carbon monoxide and hydrogen has not been absorbed any more, and usually the reaction time is in the range of 4 to 20 hours.

Carbon monoxide and hydrogen which are necessary for the reaction can be fed to the reaction vessel in the state of a mixed gas or separately. A molar ratio between carbon monoxide and hydrogen can be suitably selected, when they are fed to the reaction system. However, in the hydroformylating reaction in the hydroformylation step of the present invention, carbon monoxide and hydrogen are absorbed and consumed in a molar ratio of 1:1 accurately. Therefore, the feed of carbon monoxide and hydrogen in a molar ratio of 1:1 is most effective, depending upon the size of the reaction vessel and the system of the reaction.

In the hydroformylation step of the present invention, a solvent which is inert to the hydroformylation can be used with the view of removing reaction heat, and the like. Examples of the solvent which is inert to the hydroformylation include polar solvents such as ethers, ketones and alcohols as well as nonpolar solvents such as paraffins, cycloparaffins and aromatic hydrocarbons. Even under solvent-free conditions, however, sufficiently satisfactory effects can usually be obtained.

After completion of the hydroformylation reaction, the reaction product is separated by distillation preferably under reduced pressure, so that the solvent can be easily removed therefrom. The thus recovered complex catalyst can be used again.

It is important that the hydroformylation is carried out at the reaction temperature and under reaction pressure in the above-mentioned respective ranges. When these conditions deviate from these ranges, particularly when the reaction temperature or reaction pressure is higher than the above limited range, 4-(2'-methyl-1'-propenyl)ethylbenzene and 4-(2'-methyl-2'-propenyl)ethylbenzene of the olefin by-products in the group A react sometimes, and furthermore 4-(2'-methyl-1'-propenyl)vinylbenzene and 4-(2'-methyl-2'-propenyl)vinylbenzene are carbonylated unpreferably not only on the vinyl groups thereof but also on the substituted propenyl groups thereof.

If p-isobutylstyrene is fed to the carbonylation step (II) in the form of its mixture containing any one of the olefin by-products in the group A, an unsaturated aldehyde having an ethylenic double bond in the following group B is formed as a by-product in addition to α-(4-isobutylphenyl)propionaldehyde:

Group B:
and
α-[4-(2'-methyl-1'-propenyl)phenyl]propionaldehyde
α-[4-(2'-methyl-2'-propenyl)phenyl]propionaldehyde.

As described above, 4-(2'-methyl-2'-propenyl)ethylbenzene and 4-(2'-methyl-2'-propenyl)ethylbenzene scarcely react under the carbonylation reaction conditions of the present invention, and as a result, they are present as unreacted components in the carbonylated product.

The unreacted olefins which contain 4-(2'-methyl-1'-propenyl)ethylbenzene and 4-(2'-methyl-2'-propenyl)ethylbenzene and in which the unreacted p-isobutylstyrene is present can be easily separated and recovered, since boiling points of these components are different from those of the produced aldehydes. All of these unreacted olefins can be converted into p-isobutylethylbenzene by hydrogenation in a usual manner. This hydrogenation can be achieved by the same procedure as in the hydrogenation of the olefin by-products in the group A which has been already described in the previous hyrogenation step.

p-Isobutylethylbenzene obtained by hydrogenating the unreacted olefins can be recycled partially or wholly as the raw material in the dehydrogenation step (I).

After the hydroformylation, if necessary, α-(4-isobutylphenyl)propionaldehyde and the aldehydes in the group B may be separated by distillation. The separated α-(4-isobutylphenyl)propionaldehyde can be easily converted into α-(4-isobutylphenyl)propionic acid by oxidation in a usual manner which will be described hereinafter.

With regard to the aldehyde in the group B, hydrogenation is given thereto, so that the ethylenic double bond alone in the substituted propenyl group of the aldehyde is selectively hydrogeneated. In this way, α-(4-isobutylphenyl)propanaldehyde which is the desired compound of phenyl)propionaldehyde which is the desired compound of the hydroformylation step can be prepared from the aldehyde by-product in the carbonylation step.

This selective hydrogenation can be carried out in the presence of a suitable hydrogenating agent, for example, a hydrogenating metal such as lithium aluminum hydride in a usual manner. Alternatively, the hydrogenation can be also performed by the reaction with hydrogen in the presence of the hydrogenating metal catalyst, as in the case of the technique of hydrogenating the olefin by-product in the above-mentioned group A.

If the hydrogenation process in which the selectivity is not so high is employed at the time of the hydrogenation of the unsaturated aldehyde, the carbon-carbon double bond of the aldehyde is predominantly reduced, but simultaneously the aldehyde group also tends to be reduced.

Similarly in the case that the unsaturated aldehyde in the group B is reacted with hydrogen in the presence of the above-mentioned hydrogenating metallic catalyst, the unsaturated aldehyde is hydrogenated not only on the carbon-carbon double bond in the substituted propenyl group thereof but also on the carbon-oxygen double bond in the formyl group thereof by employing high-pressure hydrogen or a high hydrogenation temperature to form 2-(4-isobutylphenyl)propanol, depending upon the kind of metallic catalyst. For example, when the compound in the group B is hydrogenated with Ni-Cr$_2$O$_3$-acidic china clay or 5% Pd-Al$_2$O$_3$, α-(4-isobutylphenyl)propionaldehyde can be obtained in a high yield, and if reaction conditions are made more rigorous, the production of 2-(4-isobutylphenyl)propanol increases. However, the ability of Pd to hydrogenate the formyl group is usually poor, and therefore α-(4-isobutylphenyl)propionaldehyde is mainly produced, but the ability of Pt, Ni or Cu to hydrogenate the formyl group is high, and thus 2-(4-isobutylphenyl)propanol increases. In this connection, under such conditions that the unsaturated aldehyde is severely reduced as far as 2-(4-isobutylphenyl)propanol, α-(4-isobutylphenyl)propionaldehyde is also usually reduced and converted into 2-(4-isobutylphenyl)propanol.

However, in the present invention, the production of 2-(4-isobutylphenyl)propanol involves no problem, because 2-(4-isobutylphenyl)propanol can be easily converted into α-(4-isobutylphenyl)propionic acid by oxidizing its hydroxyl group in a known manner, in other words because this alcohol is the precursor of the α-(4-isobutylphenyl)propionic acid. Conveniently, this oxidation can be accomplished by the same procedure as in the oxidation technique of α-(4-isobutylphenyl)propionaldehyde to an acid.

Thus, the hydrogenation can be given to the mixture of α-(4-isobutylphenyl)propionaldehyde and the unsaturated aldehyde in the group B. Therefore, in order to hydrogenate the unsaturated aldehyde in the group B, there can be also utilized a manner in which the selectivity to the reduction of the carbon-carbon double bond is not so high, for example, the above-mentioned manner of hydrogenating the olefin by-product in the group A.

In consequence, the preferable hydrogenation manner in the present invention comprises directly hydrogenating the carbonylated material without any treatment, or alternatively first recovering α-(4-isobutylphenyl)propionaldehyde in the form of a mixture containing the unsaturated aldehyde in the group B by simple distillation, and then hydrogenating this mixture. This hydrogenation is carried out so as to hydrogenate at least carbon-carbon double bond in the substituted propenyl group of the aldehyde in the group B. A more preferable hydrogenation manner comprises selectively hydrogenating the carbon-carbon double bond alone in the substituted propenyl group of the aldehyde in the group B present in the mixture. If the hydrogenation is selectively performed in such a manner, the resulting product is only α-(4-isobutylphenyl)propionaldehyde.

As the oxidation manner of oxidizing the carboxyl group in the hydroxyl group or formyl group of α-(4-isobutylphenyl)propionaldehyde or 2-(4-isobutylphenyl)propanol obtained in the carbonylation step or the subsequent hydrogenation step in order to form α-(4-isobutylphenyl)propionic acid, any conventional oxidation procedure can be used. Since the 2-(4-isobutylphenyl)propanol is a primary alcohol, the oxidation of the alcohol can be achieved by employing a usual oxidation technique by which such a kind of primary alcohol is oxidized and converted into a carboxylic acid. In particular, a manner using an oxidizing agent such as $K_2Cr_2O_7$, $KMnO_4$, NaOCl, NaOBr or NaOI is preferable, since when such a manner is used, the yield of α-(4-isobutylphenyl)propionic acid is high. In the case that the phase of the oxidation reaction becomes a liquid-liquid ununiformed phase, depending upon kinds of oxidizing agent and solvent, a phase transfer catalyst such as methyltrioctylammonium chloride is also effective in the oxidation reaction of the present invention. Moreover, an oxidation manner of oxidizing α-(4-isobutylphenyl)propionaldehyde so as to covert the latter into α-(4-isobutylphenyl)propionic acid is also utilized, as in the case of the oxidation procedure of 2-(4-isobutylphenyl)propanol. In this case, the amount of the oxidizing agent is about half an amount of an oxidizing agent necessary to oxidize 2-(4-isobutylphenyl)propanol to α-(4-isobutylphenyl)propionic acid. In any case, the reaction temperature in the oxidation step is usually less than room temperature, preferably 0° C. or less. When the reaction temperature is higher than this level, secondary reactions such as the oxidation of an isobutyl group increase unpreferably.

Carbonylation (hydrocarboxylation or hydroesterification)

Next, reference will be made to a method for converting p-isobutylstyrene into α-(4-isobutylphenyl)pronionic acid or its alkyl ester by hydrocarboxylation or hydroesterification.

In the hydrocarboxylation reaction, p-isobutylstyrene is reacted with carbon monoxide and water to form α-(4-isobutylphenyl)propionic acid. Moreover, in the hydroesterification reaction, p-isobutylstyrene is reacted with carbon monoxide and an optional lower alcohol having a lower alkyl group to form an alkyl ester of α-(4-isobutylphenyl)propionic acid. For example, when methyl alcohol is used, methyl α-(4-isobutylphenyl)propionate.

Under specific reaction conditions of the hydrocarboxylation or hydroesterification, the olefin by-product in the group A reacts as follows: 4-(2'-Methyl-1'-propenyl)ethylbenzene and 4-(2'-methyl-2'-propenyl)ethylbenzene scarcely react.

On the other hand, under the specific reaction conditions of the present invention, 4-(2'-methyl-1'-propenyl)vinylbenzene and 4-(2'-methyl-2'-propenyl)vinylbenzene are substantially hydrocarboxylated or hydroesterified only on the vinyl group thereof, and the substituted propenyl group thereof scarcely changes.

That is, 4-(2'-methyl-1'-propenyl)vinylbenzene is hydrocarboxylated or hydroesterified to α-[4-(2'-methyl-1'-propenyl)phenyl]propionic acid or its alkyl ester, and 4-(2'-methyl-2'-propenyl)vinylbenzene is hydrocarboxylated or hydroesterified to α-[4-(2'-methyl-2'-propenyl)phenyl]propionic acid or its alkyl ester.

Whether the target of the hydrocarboxylation or hydroesterification is the olefin by-product alone in the above-mentioned group A or an olefin mixture of p-isobutylstyrene and the olefin by-product, similar reaction results will be obtained under the specific reaction conditions of the present invention.

Examples of the transition metal complex catalyst used in the above-mentioned hydrocarboxylation or hydroesterification are complex catalysts of transition metals such as palladium, rhodium and iridium, and the particularly preferable catalyst is the complex of palladium. The transition metal has a ligand, and therefore it is used in the form of the transition metal containing the ligand. Examples of the ligand are halogen atoms, trivalent phosphorus compounds and carbon monoxide, but the latter carbon monoxide is used in the form of a carbonyl complex. As described above, the transition metal can be used, but in the case of palladium, what has any valency of 0 to 2 can be used.

Typical examples of the catalyst for the hydrocarboxylation or hydroesterification include bistriphenylphosphinedichloro complex, bistributylphosphinedichloro complex, bistricyclohexylphosphinedichloro complex, π-allyltriphenylphosphinedichloro complex, triphenylphosphinepiperidinedichloro complex, bisbenzonitriledichloro complex, biscyclohexyloximedichloro complex, 1,5,9-cyclododecatriene-dichloro complex, bistriphenylphosphinedicarbonyl complex, bistriphenylphosphine acetate complex, bistriphenylphosphine dinitrate complex, bistriphenylphosphine sulfate complex, tetrakistriphenylphosphine complex, chlorocarbonylbistriphenylphosphine complex having carbon monoxide as a part of a ligand, hydridocarbonyltristriphenylphosphine complex, bischlorotetracarbonyl complex and dicarbonylacetyl acetonate complex.

The catalyst can be used by feeding the same to a reaction system in the form of the complex, or alternatively, a compound which will be a ligand is separately fed to the reaction system, and the complex is formed therefrom in the system and then used as the catalyst.

The amount of the complex catalyst or the compound capable of forming the complex within the reaction system is from 0.0001 to 0.5 mol, preferably 0.001 to 0.1 mol, with respect to 1 mol of an olefin such as p-isobutylstyrene. Furthermore, the amount of the compound which will be the ligand is from 0.8 to 10 mols, preferably 1 to 4 mols with respect to 1 mol of the transition metal which will be the nucleus of the complex such as palladium, rhodium or iridium.

For the purpose of accelerating the reaction, an inorganic halide such as hydrogen chloride or boron trifluoride may be added to the reaction system.

The amount of such a halide is from 0.1 to 30-fold mols, preferably 1 to 15-fold mols in terms of a halogen atom with regard to 1 mol of the complex catalyst or the compound capable of forming the complex. When the amount of the halide is less than 0.1 mol, the effect of the added halide is not perceptible sometimes, depending upon the kind of catalyst. When it is in excess of 30-fold mols, the activity of the catalyst deteriorates reversely, and a halogen atom is added to the double bond of p-isobutylstyrene, so that the intended reaction is inhibited unpreferably.

The hydrocarboxylation or hydroesterification reaction is carried out at a temperature of 40° to 250° C., preferably 70° to 120° C. When the reaction temperature is less than 40° C., a reaction rate is too low to actually achieve the hydrocarboxylation or hydroesterification. When it is more than 250° C., polymerization reaction and the decomposition of the complex catalyst occur unpreferably.

The reaction pressure is 5 kg/cm$^2$ or more. When the pressure is less 5 kg/cm$^2$, a reaction rate is too low to actually achieve the hydrocarboxylation or hydroesterification. The higher the pressure of carbon monoxide is, the faster the reaction proceeds, but when the pressure is too high, it is required to sufficiently heighten the pressure resistance of a reactor. Therefore, it is natural that the upper limit of the reaction pressure is present, and it is 600 kg/cm² in practice.

The reaction is allowed to proceed until carbon monoxide is not absorbed any more, and the reaction time is usually in the range of 4 to 20 hours.

Examples of the usable alcohol include lower alcohols having 1 to 4 carbon atoms such as methyl alcohol, ethyl alcohol, n-propyl alcohol, isopropyl alcohol, n-butyl alcohol, sec-butyl alcohol and isobutyl alcohol, and above all, methyl alcohol is preferable.

After completion of the hydrocarboxylation or hydroesterification reaction, the catalyst can be easily separated from the reaction product by extraction or distillation. The recovered complex catalyst can be reused.

It is important that the hydrocarboxylation or hydroesterification is carried out under conditions of the reaction temperature, reaction pressure and the like in the above-mentioned respective ranges. When these conditions deviate from these ranges, particularly when the reaction temperature or reaction pressure is higher than the above limited range, 4-(2'-methyl-1'-propenyl)ethylbenzene and 4-(2'-methyl-2'-propenyl)ethylbenzene of the olefin by-products in the group A react sometimes, and furthermore 4-(2'-methyl-1'-propenyl)vinylbenzene and 4-(2'-methyl-2'-propenyl)vinylbenzene are carbonylated unpreferably not only on the vinyl groups thereof but also on the substituted propenyl groups thereof.

In the hydrocarboxylation step, α-(4-isobutylphenyl)propionic acid is obtained from p-isobutylstyrene. Furthermore, in the hydroesterification step, α-(4-isobutylphenyl)propionic acid obtained from p-isobutylstyrene is esterified to form an alkyl ester, and the latter is then easily converted into α-(4-isobutylphenyl)propionic acid by hydrolysis in the presence of an acid or alkali catalyst in a usual manner.

In the case that the olefin mixture of p-isobutylstyrene and the olefin by-product in the group A is hydrocarboxylated or hydroesterified under the specific conditions of the present invention, any one of unsaturated compounds in the following group C is formed in addition to α-(4-isobutylphenyl)pronionic acid or its alkyl ester:

Group C:
α-[4-(2'-methyl-1'-propenyl)phenyl]propionic acid or its alkyl ester and
α-[4-(2'-methyl-2'-propenyl)phenyl]propionic acid or its alkyl ester.

Therefore, p-isobutylstyrene in the olefin mixture is hydrocarboxylated or hydroesterified, and α-(4-isobutylphenyl)propionic acid or its alkyl ester is then recovered. On the other hand, the unsaturated propionic acid or its alkyl ester of the by-products in the group C is hydrogenated on the substituted propenyl group thereof so as to be easily converted into α-(4-isobutylphenyl)propionic acid or its alkyl ester which is the desired compound of this carbonylation step. This procedure is beneficial, since the unsaturated by-product in the group C can be also converted into the desired compound.

Moreover, the hydrogenation can be also given to the mixture containing α-(4-isobutylphenyl)propionic acid or its alkyl ester and the unsaturated compound in the group C.

This hydrogenation can be achieved by the same procedure as in the hydrogenation technique of the olefin by-product in the above-mentioned group A. That is, the hydrogenation is carried out by the use of a suitable hydrogenating agent such as a metal hydride, but in general, by reaction with hydrogen in the presence of a hydrogenating metallic catalyst. The hydrogenating catalyst in the hydrogenation step can be suitably selected from the conventional known hydrogenating metallic catalysts which hydrogenate an ethylenic carbon-carbon unsaturated double bond but are inert to the nucleus of an aromatic ring.

Typical examples of these catalysts include metallic catalysts containing at least one of metals such as Fe, Co, Ni, Ru, Rh, Pd, Os, Ir, Pt, Cu, Re, Mo, W, Cr and Ta. These metallic catalysts, when used, can be supported on a suitable carrier such as silica, silica-alumina, pumice stone or carbon. Reaction conditions of the hydrogenation can be suitably selected, taking an activity of the catalyst into consideration, on condition that the nucleus of the aromatic ring is not hydrogenated. In general, the reaction temperature of the hydrogenation is from ordinary temperature to 300° C., and a hydrogen pressure is from atmospheric pressure to 300 kg/cm².

As described above, in the carbonylation step of the olefin mixture, 4-(2'-methyl-1'-propenyl)ethylbenzene and 4-(2'-methyl-2'-propenyl)ethylbenzene do not react substantially, and as a result, they are present as unreacted components in the reaction product. These unreacted components can be easily separated and recovered by usual distillation, since boiling points of these components are different from a boiling point of the produced acid or ester. All of these unreacted olefins can be converted into p-isobutylethylbenzene by hydrogenation. This hydrogenation can be achieved by the same procedure as in the hydrogenation of the olefin by-products in the group A which has been already described. The thus recovered p-isobutylethylbenzene can be recycled partially or wholly as the raw material in the dehydrogenation step.

After the hydrogenation, if necessary, α-(4-isobutylphenyl)propionaldehyde or its alkyl ester is recovered by distillation. The alkyl α-(4-isobutylphenyl)propionate is then hydrolyzed in a usual manner in order to obtain α-(4-isobutylphenyl)propionic acid, as described above.

The thus obtained α-(4-isobutylphenyl)propionic acid can be suitably recrystallized.

The present invention permits industrially and economically preparing α-(4-isobutylphenyl)propionic acid and its precursor, i.e., alkyl α-(4-isobutylphenyl)propionate or α-(4-isobutylphenyl)propionaldehyde by selectively dehydrogenating the ethyl group of p-isobutylethylbenzene; converting the latter into p-isobutylstyrene effectively; and selectively carbonylating the obtained p-isobutylstyrene fraction.

When the dehydrogenation of p-isobutylethylbenzene is carried out under specific conditions in the dehydrogenation step of the present invention, p-isobutylstyrene can be prepared in a high selectivity coefficient. Therefore, high-purity p-isobutylstyrene and unreacted p-isobutylethylbenzene can be prepared only by subjecting the dehydrogenated reaction mixture obtained by the method of the present invention to two or three simple unit operations such as the separation from a water layer, drying and distillation.

Furthermore, the unreacted p-isobutylethylbenzene can be recovered and reused as the raw material for the dehydrogenation. On the other hand, olefin by-products in the dehydrogenation step, i.e., 4-(2'-methyl-1'-propenyl)ethylbenzene, 4-(2'-methyl-1'-propenyl)vinylbenzene, 4-(2'-methyl-2'-propenyl)ethylbenzene and 4-(2'-methyl-2'-propenyl)vinylbenzene are, after separation, converted into p-isobutylethylbenzene by the hydrogenation, and this product can be reused as the raw material for the dehydrogenation in the dehydrogenation step (I).

The carbonylated reaction mixture obtained in the carbonylation step (II) can be separated and recovered by a simple distillation under reduced pressure or extraction, so that high-purity α-(4-isobutylphenyl)propionic acid and its precursor, i.e., alkyl α-(4-isobutylphenyl)propionate or α-(4-isobutylphenyl)propionaldehyde can be separated and recovered.

In the present invention, an olefin mixture containing an olefin by-product of group A in addition to the p-isobutylstyrene fraction can be fed to the carbonylation step (II). In this case, a reaction mixture obtained in the carbonylation step (II) can be hydrogenated directly without any treatment or after a suitable simple distillation. Secondary carbonylated product which is formed in the carbonylation of the olefin mixture containing the secondary olefin, i.e., α-[4-(2'-methyl-1'-propenyl)phenyl)]propionic acid or its alkyl ester or α-[4-(2'-methyl-2'-propenyl)phenyl]propionic acid or its alkyl ester can be easily converted, by the hydrogenation, into α-(4-isobutylphenyl)propionic acid or its alkyl ester which is the desired compound in the carbonylation step.

When α-[4-(2'-methyl-1'-propenyl)phenyl]propionaldehyde and α-[4-(2'-methyl-2'-propenyl)phenyl]-propionaldehyde which are the by-products in the hydroformylation step are selectively hydrogenated, α-(4-isobutylphenyl)propionaldehyde is obtained. Furthermore, such by-products can be converted into 2-(4-isobutylphenyl)propanol by the hydrogenation. α-(4-Isobutylphenyl)propionaldehyde or 2-(4-isobutylphenyl)propanol can be easily similarly oxidized, so that α-(4-Isobutylphenyl)propionic acid which is the desired compound can be obtained.

Therefore, in the present invention, it is not necessary to accurately distill p-isobutylstyrene after the dehydrogenation. In addition, the by-products in the dehydrogenation and the carbonylation step can be also recovered effectively as the desired compound.

EXAMPLES

Method for Preparing α-(4-Isobutylphenyl)propionaldehyde:

As described in the undermentioned examples, dehydrogenation step, hydroformylation step and hydrogenation step were carried out.

Preparation of p-isobutylstyrene:

Experimental Example 1

An iron oxide dehydrogenating catalyst containing potassium and chromium as promotors (trade name G-64A; made by Nissan Gardlar Co., Ltd.) was regulated so as to have a grain diameter of 1 to 2 mm, and a stainless steel pipe having an inner diameter of 12 mm and a length of 1 m was filled with 20 ml of the dehydrogenating catalyst.

p-Isobutylethylbenzene (hereinafter referred to as "PBE" at times) was dehydrogenated by passing PBE itself and water through a preheating pipe and the catalyst layer at a temperature of 550° C. (a contact time with the catalyst was 0.2 second, and a molar ratio of steam to p-isobutylethylbenzene was 93), flow rates of PBE and water being 10 ml/hour and 90 ml/hour, respectively. The dehydrogenated material was then cooled, and a gas and water were separated out. Afterward, the resulting organic phase was inspected by gas chromatography to confirm the conversion of p-isobutylethylbenzene and the selectivity of p-isobutylstyrene (hereinafter referred to as "PBS" at times).

The organic phase of the dehydrogenated material was principally composed of PBE, PBS, 4-(2'-methyl-1'-propenyl)vinylbenzene (hereinafter referred to as "1-MPE" at times), 4-(2'-methyl-2'-propenyl)ethylbenzene (hereinafter referred to as "2-MPE" at times), 4-(2'-methyl-1'-propenyl)ethylbenzene (hereinafter referred to as "1-MPV") and 4-(2'-methyl-2'-propenyl)vinylbenzene (hereinafter referred to as "2-MPV"), and the composition of the same is as follows:

TABLE 1

| Component | Content |
| --- | --- |
| PBE | 69.3 wt % |
| PBS | 24.7 wt % |
| 1-MPE | 0.6 wt % |
| 2-MPE | 1.6 wt % |
| 1-MPV | 0.9 wt % |
| 2-MPV | 2.1 wt % |
| Unidentified | 0.8 wt % |

It was confirmed from the above data that the conversion of PBE was 31% and the selectivity of PBS was 83%, which means that PBS was formed by the dehydrogenation in the high selectivity.

The respective components were separated from the dehydrogenated material and then identified by mass spectrometry, IR and proton NMR. As a result, it was confirmed that p-isobutylethylbenzene was all the same as what had been used as the raw material and the production of sec-butylbenzene and tert-butylbenzene was not perceived, which means that secondary reaction such as the isomerization of an isobutyl group did not take place. As for PBS, its butyl group was an isobutyl group, which was present at the p-position.

Experimental Examples 2 to 5

Following the same procedure as in Experimental Example 1, dehydrogenation reaction was carried out, changing reaction temperature. The obtained results are set forth in Table 2 together with the results of Experimental Example 1.

TABLE 2

| Experimental Example | 2 | 3 | 1 | 4 | 5 |
| --- | --- | --- | --- | --- | --- |
| Reaction Temp. (°C.) | 450 | 500 | 550 | 600 | 650 |
| Contact Time (sec.) | 0.2 | 0.2 | 0.2 | 0.2 | 0.2 |
| Steam Ratio | 93 | 94 | 92 | 93 | 94 |
| PBE Conversion (%) | 1 | 6 | 31 | 75 | 96 |
| PBS Selectivity (%) | 99 | 98 | 83 | 51 | 7 |

Experimental Examples 6 to 10

Following the same procedure as in Experimental Example 1, dehydrogenation reaction was carried out, changing contact time. The obtained results are set forth in Table 3.

TABLE 3

| Experimental Example | 6 | 7 | 8 | 9 | 10 |
|---|---|---|---|---|---|
| Reaction Temp. (°C.) | 550 | 550 | 550 | 550 | 550 |
| Contact Time (sec.) | 0.06 | 0.10 | 0.21 | 0.28 | 0.38 |
| Steam Ratio | 96 | 98 | 96 | 94 | 96 |
| PBE Conversion (%) | 21 | 33 | 37 | 47 | 54 |
| PBS Selectivity (%) | 89 | 84 | 79 | 73 | 69 |

Experimental Examples 11 to 15

Following the same procedure as in Experimental Example 1, dehydrogenation reaction was carried out, using a copper-chromium dehydrogenating catalyst which was composed of 43% by weight of CuO, 42% by weight of $Cr_2O_3$ and 15% by weight of $SiO_2$, and changing reaction temperature. The obtained results are set forth in Table 4.

TABLE 4

| Experimental Example | 11 | 12 | 13 | 14 | 15 |
|---|---|---|---|---|---|
| Reaction Temp. (°C.) | 450 | 500 | 550 | 600 | 650 |
| Contact Time (sec.) | 0.2 | 0.2 | 0.2 | 0.2 | 0.2 |
| Steam Ratio | 93 | 94 | 92 | 93 | 94 |
| PBE Conversion (%) | 5 | 8 | 20 | 50 | 92 |
| PBS Selectivity (%) | 80 | 79 | 74 | 58 | 5 |

Experimental Examples 16 to 20

Following the same procedure as in Experimental Example 1, dehydrogenation reaction was carried out, using a copper-chromium dehydrogenating catalyst which was composed of 18% by weight of $Cr_2O_3$, 39% by weight of CuO and 38% by weight of ZnO. The obtained results are set forth in Table 5.

TABLE 5

| Experimental Example | 16 | 17 | 18 | 19 | 20 |
|---|---|---|---|---|---|
| Reaction Temp. (°C.) | 450 | 500 | 550 | 600 | 650 |
| Contact Time (sec.) | 0.2 | 0.2 | 0.2 | 0.2 | 0.2 |
| Steam Ratio | 93 | 93 | 94 | 93 | 93 |
| PBE Conversion (%) | 2 | 6 | 12 | 21 | 45 |
| PBS Selectivity (%) | 78 | 76 | 72 | 64 | 47 |

Experimental Example 21

Following the same procedure as in Experimental Example 1 with the exception that the metal of the dehydrogenating catalyst was replaced with each of metals in the following table, dehydrogenation reaction was carried out. In every case, the metal was used in the form of an oxide and supported on silica. The obtained results are set forth in the following table.

| Metal | Conversion (%) | Selectivity (%) |
|---|---|---|
| Ag | 31 | 62 |
| Cd | 12 | 64 |
| Cr | 22 | 61 |
| Zn | 13 | 52 |
| Mo | 16 | 53 |
| W | 11 | 59 |
| Mn | 11 | 61 |
| Tc | 12 | 60 |
| Re | 20 | 57 |
| Ru | 17 | 68 |
| Os | 12 | 70 |
| Co | 21 | 59 |
| Rh | 32 | 48 |
| Ir | 25 | 51 |
| Ni | 48 | 41 |
| Pd | 46 | 43 |
| Pt | 44 | 40 |

Preparation of α-(4-isobutylphenyl)propionaldehyde and hydrogenation of olefin product Experimental Example 22

One kilogram of the dehydrogenated reaction mixture obtained in Experimental Example 4 was separated by distillation into 833 g of the fraction of PBE and PBS, 116 g of the fraction of ethylbenzene and vinylbenzene, having a substituted propenyl group respectively, and 51 g of a residue. This fraction of ethylbenzene and vinylbenzene having the substituted propenyl group was analyzed by gas chromatography, and the results are set forth in Table 6

TABLE 6

| Component | Content |
|---|---|
| PBS | 10.3 wt % |
| 1-MPE | 8.6 wt % |
| 2-MPE | 21.6 wt % |
| 1-MPV | 11.2 wt % |
| 2-MPV | 29.3 wt % |
| Unidentified | 19.0 wt % |

In a 200-milliliter autoclave were placed 100 g of this fraction of ethylbenzene and vinylbenzene having the substituted propenyl group and 5 g of palladium black (a catalyst in which 5% of palladium was supported), and reaction was then performed at a reaction temperature of 50° C. under a hydrogen pressure of 20 kg/cm², until hydrogen had not been absorbed any more. Afterward, the used catalyst was removed from the resulting reaction mixture by filtration, and the obtained filtrate was then analyzed by gas chromatography. The results are set forth in Table 7.

TABLE 7

| Component | Content |
|---|---|
| PBE | 80.7 wt % |
| Unidentified | 19.3 wt % |

The mixture which has undergone the hydrogenation reaction was then distilled to prepare 71.2 g of p-isobutylethylbenzene having a purity of 99.7%.

Experimental Example 23

In a 200-milliliter autoclave equipped with a stirrer were placed 121.5 g of the dehydrogenated reaction solution obtained in Experimental Example 1 and 0.3 g of rhodium-hydridcarbonyltristriphenylphosphine, and the solution was then heated up to 60° C. with stirring. Afterward, an equimolar mixed gas of hydrogen and carbon monoxide was fed to the solution so that a pressure of 50 kg/cm² might be reached, and reaction was then continued until the mixed gas had not been absorbed any more.

After completion of the reaction, the reaction mixture was cooled to room temperature and then recovered, and it was then analyzed by gas chromatography. As a result, it was found that the conversion of p-isobutylstyrene was 99.8% and the selectivity of α-(4-isobutylphenyl)propionaldehyde was 87.8%. The total amount of hydroformylated compounds which were formed by hydroformylating substituted propenyl groups of 4-(2'-methyl-1'-propenyl)ethylbenzene, 4-(2'-methyl-2'-propenyl)ethylbenzene, 4-(2'-methyl-1'-propenyl)vinylbenzene and 4-(2'-methyl-2'-propenyl)-vinylbenzene in the reaction mixture was 1% by weight or less. Afterward, the reaction mixture was subjected to simple distillation under reduced pressure to separate the used catalyst therefrom, and the resulting distillate was then put in a 200-milliliter autoclave together with 5 g of palladium black (a catalyst in which 5% of palladium was supported). Successively, reaction was carried out at a reaction temperature of 50° C. under a hydrogen pressure of 20 kg/cm² until hydrogen had not been absorbed any more. After completion of the reaction, the catalyst was removed from the reaction mixture by filtration, and the resulting filtrate was then analyzed by gas chromatography. The results are set forth in Table 8.

TABLE 8

| Component | Content |
| --- | --- |
| PBE | 68.1 wt % |
| α-(4-isobutylphenyl)propionaldehyde | 28.0 wt % |
| Balance | 3.9 wt % |

The total amount of 1-MPE, 2-MPE, 1-MPV and 2-MPV as well as hydroformylated compounds which were formed by hydroformylating substituted propenyl groups of 1-MPE, 2-MPE, 1-MPV and 2-MPV was 1% by weight or less.

The above-mentioned filtrate was distilled under reduced pressure to obtain 28 g of α-(4-isobutylphenyl)-propionaldehyde having a boiling point of 70° to 76° C./3 mmHg. The purity of this α-(4-isobutylphenyl)-propionaldehyde was 99.8% by weight. Furthermore, the structure of the product was confirmed by comparing the results of IR analysis with standards.

Experimental Example 24

The same procedure as in Experimental Example 23 was repeated with the exception that rhodiumhydridcarbonyltristriphenylphosphine was replaced with 0.1 g of rhodium oxide and 0.6 g of triphenylphosphine, in order to perform hydroformylation. In this case, the conversion of p-isobutylstyrene was 99.8%, and the selectivity of α-(4-isobutylphenyl)propionaldehyde was 87.2%. The total amount of hydroformylated compounds which were formed by hydroformylating substituted propenyl groups of 4-(2'-methyl-1'-propenyl)ethylbenzene, 4-(2'-methyl-2'-propenyl)ethylbenzene, 4-(2'-methyl-1'-propenyl)vinylbenzene and 4-(2'-methyl-2'-propenyl)vinylbenzene in the reaction mixture was 1% by weight or less.

Experimental Example 25

One kilogram of the dehydrogenated reaction mixture obtained in Experimental Example 4 was separated by simple distillation into 52.2 g of the PBE fraction, 441 g of the fraction of PBS, and ethylbenzene and vinylbenzene having a substituted propenyl group, and 35 g of a residue. The fraction of PBS and ethylbenzene and vinylbenzene having the substituted propenyl group was then analyzed by gas chromatography, and the results are set forth in Table 9.

TABLE 9

| Component | Content |
| --- | --- |
| PBE | 4.8 wt % |

TABLE 9-continued

| Component | Content |
| --- | --- |
| PBS | 72.6 wt % |
| 1-MPE | 2.0 wt % |
| 2-MPE | 5.7 wt % |
| 1-MPV | 2.9 wt % |
| 2-MPV | 7.5 wt % |
| Unidentified | 4.5 wt % |

In a 200-milliliter autoclave were placed 100 g of this fraction and 1.0 g of rhodiumhydridcarbonyltristriphenylphosphine, and they were then heated up to 60° C. with stirring. Afterward, an equimolar mixed gas of hydrogen and carbon monoxide was fed to the solution so that a pressure of 50 kg/cm² might be reached, and reaction was then continued until the mixed gas had not been absorbed any more.

After completion of the reaction, the reaction mixture was cooled, recovered, and then subjected to simple distillation under reduced pressure to separate the used catalyst therefrom. Afterward, the resulting distillate was put in a 200-milliliter autoclave together with 5 g of palladium black (a catalyst in which 5% of palladium was supported), and reaction was then carried out at a reaction temperature of 50° C. under a hydrogen pressure of 20 kg/cm² until hydrogen had not been absorbed any more. After completion of the reaction, the catalyst was removed from the reaction mixture by filtration, and the resulting filtrate was then analyzed by gas chromatography. The results are set forth in Table 10.

TABLE 10

| Component | Content |
| --- | --- |
| PBE | 10.0 wt % |
| α-(4-isobutylphenyl)propionaldehyde | 75.7 wt % |
| Balance | 14.3 wt % |

The total amount of 1-MPE, 2-MPE, 1-MPV and 2-MPV as well as hydroformylated compounds which were formed by hydroformylating substituted propenyl groups of 1-MPE, 2-MPE, 1-MPV and 2-MPV was 1% by weight or less.

Experimental Example 26

Following the same procedure as in Experimental Example 25, 100 g of the fraction regarding Table 9 was hydroformylated, and the resulting reaction mixture was recovered and then subjected to simple distillation under reduced pressure to separate the used catalyst therefrom. The resulting distillate was then put in a 200-milliliter autoclave together with 5 g of a copper-chromium hydrogenating catalyst reduced with hydrogen at 200° C. for 24 hours (trade name N201; made by Nikki Kagaku Co., Ltd.). Successively, reaction was carried out at a reaction temperature of 80° C. under a hydrogen pressure of 20 kg/cm² until hydrogen had not been absorbed any more. After completion of the reaction, the catalyst was removed from the reaction mixture by filtration, and the resulting filtrate was then analyzed by gas chromatography. The composition of the reaction mixture is set forth in Table 11.

TABLE 11

| Component | Content |
| --- | --- |
| PBE | 9.7 wt % |
| 2-(4-isobutylphenyl) | 76.0 wt % |

TABLE 11-continued

| Component | Content |
|---|---|
| propanol Balance | 14.2 wt % |

The total amount of 1-MPE, 2-MPE, 1-MPV and 2-MPV as well as hydroformylated and hydroxylated compounds which were formed by hydroformylating and hydroxylating substituted propenyl groups of 1-MPE, 2-MPE, 1-MPV and 2-MPV was 1% by weight or less.

Preparation of α-(4-isobutylphenyl)pronionic acid from α-(4-isobutylphenyl)propionaldehyde or 2-(4-isobutylphenyl)propanol by oxidation Experimental Example 27

In a 200-milliliter flask with a stirrer were placed 25 g of α-(4-isobutylphenyl)propionaldehyde having a boiling range of 70° to 76° C./3 mmHg obtained in Experimental Example 23, and 1 g of concentrated hydrochloric acid and 40 ml of acetone as a solvent were further put therein and these materials were cooled to −15° C. Next, while the temperature was maintained at a level of −12° C. to −16° C., 36 g of a 10% aqueous sodium hypochlorite solution was gradually added dropwise thereto. After completion of the addition, reaction was further performed with stirring for 1 hour. After the reaction had been over, a 5% aqueous sodium hydroxide solution was added to the solution so as to adjust its pH to 8.5. The mixture was allowed to stand, and a separated lower aqueous phase was then washed with normal hexane.

To this aqueous phase was added 5% hydrochloric acid to adjust its pH to 2, and a separated oil portion was extracted with normal hexane, followed by water washing. The used normal hexane was vaporized out under reduced pressure in order to obtain 26.8 g of light yellow crude α-(4-isobutylphenyl)propionic acid crystals.

The thus obtained crude α-(4-isobutylphenyl)propionic acid was then recrystallized from a normal hexane solvent to prepare 22.6 g of white purified α-(4-isobutylphenyl)propionic acid (melting point 75°-76° C.) crystals. The results of spectra and the like were in accord with standards.

Experimental Example 28

In a 200-milliliter flask with a stirrer was placed 40 g of the hydrogenated reaction mixture obtained in Experimental Example 25, and the same procedure as in Experimental Example 27 was repeated to perform oxidation, extraction and the like, so that 27.2 g of light yellow crude α-(4-isobutylphenyl)propionic acid crystals was obtained.

The thus obtain α-(4-isobutylphenyl)propionic acid was recrystallized from a normal hexane solvent in order to prepare 24.1 g of white purified α-(4-isobutylphenyl)propionic acid (melting point 75°-76° C.) crystals.

Experimental Example 29

In a 200-milliliter flask with a stirrer was placed 40 g of the hydrogenated reaction mixture obtained in Experimental Example 26, and 2 g of concentrated hydrochloric acid and 80 ml of acetone as a solvent were further put therein and they were cooled to −15° C. Next, while temperature was maintained at a level of −12 to −16° C., 72 g of a 10% aqueous sodium hypochlorite solution was gradually added dropwise thereto. After completion of the addition, reaction was further performed with stirring for 1 hour. After the reaction had been over, a 5% aqueous sodium hydroxide solution was added to the solution so as to adjust its pH to 8.5. The mixture was allowed to stand, and a separated lower aqueous phase was then washed with normal hexane.

To this aqueous phase was added 5% hydrochloric acid to adjust its pH to 2, and a separated oil portion was extracted with normal hexane, followed by water washing. The used normal hexane was vaporized out under reduced pressure in order to obtain 26.2 g of light yellow crude The thus obtained crude α-(4-isobutylphenyl)propionic acid was then recrystallized from a normal hexane solvent to prepare 20.9 g of white purified α-(4-isobutylphenyl)propionic acid (melting point 75°-76° C.) crystals.

Comparative Example 1

Following the same procedure as in Experimental Example 1, p-sec-butylethylbenzene (purity 97.5% by weight) was subjected to dehydrogenation reaction. The results are set forth in Table 12.

TABLE 12

| Reaction Temperature (°C.) | 550 |
|---|---|
| Contact Time (second) | 0.20 |
| Steam Molar Ratio | 93 |
| p-Sec-butylethylbenzene Conversion (%) | 43.4 |
| Composition of Reaction Product | |
| p-sec-butylethylbenzene | 55.4 wt % |
| p-sec-butylstyrene | 6.5 wt % |
| p-sec-butenylethylbenzene | 13.3 wt % |
| p-sec-butyenylstyrene | 14.6 wt % |
| unidentified | 10.2 wt % |

Next, a hydrocarboxylation or hydroesterification step and a hydrogenation step followed.

Preparation of α-(4-isobutylphenyl)propionic acid or its alkyl ester

Experimental Example 30 (hydrocarboxylation)

In a 500-milliliter autoclave were placed 50 g of p-isobutylstyrene having a purity of 97.8% by weight which had been purified by distilling the dehydrogenated reaction mixture prepared in Experimental Example 1, 5.5 g of bisdichlorotriphenylphosphine palladium, 80 g of a 10% aqueous hydrochloric acid solution and 80 ml of toluene as a solvent. Afterward, carbon monoxide was fed to the autoclave with stirring at ordinary temperature so that a pressure of 100 kg/cm² might be reached therein, and while the solution was then heated up to 120° C., the pressure in the autoclave was increased up to 300 kg/cm². Reaction was performed until carbon monoxide had not been absorbed any more, and additionally the reaction was further continued for 24 hours.

After completion of the reaction, the reaction mixture was recovered and then separated into an oil layer and an aqueous layer by the use of a separatory funnel. Afterward, the oil layer was extracted three times with 50 ml of a 8% aqueous sodium hydroxide solution, and the resulting aqueous extract was mixed with the above aqueous layer. Hydrochloric acid was then added to the mixture so as to adjust a pH of the latter to 2. Next, the mixture was extracted three times with 500 ml of chloroform, and the resulting extract was exposed to conditions of reduced pressure in order to distill off chloroform, thereby obtaining 52.3 g of light yellow crystals of α-(4-isobutylphenyl)propionic acid. In this case, the conversion of p-isobutylstyrene was 100%, and the selectivity of α-(4-isobutylphenyl)propionic acid was 89.0%.

Experimental Example 31

In a 500-milliliter autoclave were placed 202.43 g of the dehydrogenated material obtained in Experimental Example 1, 5.5 g of bisdichlorotriphenylphosphine palladium and 80 g of a 10% aqueous hydrochloric acid solution. Afterward, carbon monoxide was fed to the autoclave with stirring at ordinary temperature so that a pressure of 100 kg/cm$^2$ might be reached therein, and while the solution was then heated up to 120° C., the pressure in the autoclave was increased up to 300 kg/cm$^2$. Reaction was performed until carbon monoxide had not been absorbed any more, and additionally the reaction was further continued for 24 hours.

After completion of the reaction, the reaction mixture was recovered and then separated into an oil layer and an aqueous layer by the use of a separatory funnel. Afterward, the oil layer was extracted three times with 50 ml of a 8%. aqueous sodium hydroxide solution, and the resulting aqueous extract was mixed with the above aqueous layer. Hydrochloric acid was then added to the mixture so as to adjust a pH of the latter to 2. Next, the mixture was extracted three times with 500 ml of chloroform, and the resulting extract was exposed to conditions of reduced pressure in order to distill off chloroform, thereby obtaining 50.2 g of light yellow crystals of α-(4-isobutylphenyl)propionic acid. In this case, the conversion of p-isobutylstyrene was 100%, the selectivity of α-(4-isobutylphenyl)propionic acid was 87.3%, the hydrocarboxylation ratio of the substituted propenyl group of 4-(2'-methyl-1'-propenyl)ethylbenzene was 0%, the hydrocarboxylation ratio of the substituted propenyl group of 4-(2'-methyl-2'-propenyl)ethylbenzene was 0.8%, the hydrocarboxylation ratio of the substituted propenyl group of 4-(2'-methyl-1'-propenyl)vinylbenzene was 0%, and the hydrocarboxylation ratio of the substituted propenyl group of 4-(2'-methyl-2'-propenyl)vinylbenzene was 0.6%.

Experimental Example 32 (hydroesterification)

In a 200-milliliter autoclave were placed 70.4 g of p-isobutylstyrene having a purity of 97.8% by weight which had been purified by distilling the organic phase of the dehydrogenated material prepared in Experimental Example 1, 25.5 ml of methanol, 40 ml of toluene as a solvent, 0.0756 g of PdCl$_2$ as a catalyst, 0.0292 g of CuCl$_2$ as a promotor and 0.2161 g of triphenylphosphine as a ligand. Afterward, the temperature in the autoclave was elevated up to 90° C. with stirring and the pressure in the autoclave was maintained at 70 kg/cm$^2$ by feeding carbon monoxide thereto, and reaction was performed for 8 hours. After completion of the reaction, the reaction mixture was analyzed through gas chromatography, and as a result, the conversion of p-isobutylstyrene was 99.6%, and the selectivity of methyl α-(4-isobutylphenyl)propionate was 90.9%.

Experimental Example 33

In a 500-milliliter autoclave were placed 285.0 g of the organic phase of the dehydrogenated material prepared in Experimental Example 1, 25.5 ml of methanol, 0.0756 g of PdCl$_2$ as a catalyst, 0.0292 g of CuCl$_2$ as a promotor and 0.2161 g of triphenylphosphine as a ligand. Afterward, the temperature in the autoclave was elevated up to 90° C. with stirring and the pressure in the autoclave was maintained at 70 kg/cm$^2$ by feeding carbon monoxide thereto, and reaction was performed for 8 hours. After completion of the reaction, the reaction mixture was analyzed through gas chromatography, and as a result, the conversion of p-isobutylstyrene was 99.8%, the selectivity of methyl α-(4-isobutylphenyl)propionate was 88.9%, the hydroesterification ratio of the substituted propenyl group of 4-(2'-methyl-1'-propenyl)ethylbenzene was 0%, the hydroesterification ratio of the substituted propenyl group of 4-(2'-methyl-2'-propenyl)ethylbenzene was 0.6%, the hydroesterification ratio of the substituted propenyl group of 4-(2'-methyl-1'-propenyl)vinylbenzene was 0%, and the hydroesterification ratio of the substituted propenyl group of 4-(2'-methyl-2'-propenyl)vinylbenzene was 0.3%.

Experimental Example 34

In a 500-milliliter autoclave were placed 100 g of the fraction regarding Table 9, 9.4 g of bisdichlorotriphenylphosphine palladium, 137 g of a 10% aqueous hydrochloric acid solution and 140 ml of toluene as a solvent. Afterward, carbon monoxide was fed to the autoclave at ordinary temperature with stirring so that a pressure of 100 kg/cm$^2$ might be reached therein, and the pressure was further increased up to 300 kg/cm$^2$, while the temperature in the autoclave is elevated up to 120° C. Reaction was performed until carbon monoxide had not been absorbed any more, and additionally the reaction was further continued for 24 hours.

After completion of the reaction, the reaction mixture was cooled, recovered, and separated into an oil layer and an aqueous layer by the use of a separatory funnel. The oil layer was dried with anhydrous sodium sulfate and then filtered, and the resulting filtrate was then placed in a 500-milliliter autoclave together with 5 g of palladium black (a catalyst wherein 5% of palladium was supported). Reaction was performed at a reaction temperature of 50° C. under a hydrogen pressure of 20 kg/cm$^2$, until hydrogen had not been absorbed any more, and the used catalyst was removed from the reaction mixture by filtration. The resulting filtrate was then analyzed through gas chromatography, and contents of components other than toluene were set forth in Table 13.

TABLE 13

| Component | Content |
| --- | --- |
| PBE | 9.8 wt % |
| α-(4-isobutylphenyl) propionic acid | 74.1 wt % |
| Others | 16.1 wt % |

In the hydrogenated reaction mixture, the total amount of 1-MPE, 2-MPE, 1-MPV and 2-MPV as well as hydrocarboxylated compounds formed by hydrocarboxylating substituted propenyl groups of 1-MPE, 2-MPE, 1-MPV and 2-MPV was 1% by weight or less.

Experimental Example 35

In a 500-ml autoclave were placed 100 g of the fraction regarding Table 9, 31 ml of methanol, 50 ml of toluene as a solvent, 0.0921 g of PdCl$_2$ as a catalyst, 0.0355 g of CuCl$_2$ as a promotor and 0.2637 g of triphenylphosphine as a ligand. The temperature in the autoclave was elevated up to 90° C. with stirring, and carbon monoxide was fed to the autoclave so that the pressure therein might be maintained at 70 kg/cm$^2$, and reaction was performed for 8 hours. After the reaction, the reaction mixture was cooled and recovered, the used catalyst was separated and removed by distillation under reduced pressure. Afterward, the reaction mixture was then placed in a 500-milliliter autoclave together with 10 g of palladium black (a catalyst wherein 5% of palladium was supported), reaction was then performed at a reaction temperature of 50° C. under a hydrogen pressure of 20 kg/cm$^2$, until hydrogen had not been absorbed any more. The palladium black catalyst was removed from the reaction mixture by filtration, and the resulting filtrate was analyzed through gas chromatography, and contents of components other than toluene were as shown in Table 14.

TABLE 14

| Component | Content |
| --- | --- |
| PBE | 9.4 wt % |
| α-(4-isobutylphenyl) propionic acid | 74.2 wt % |
| Others | 16.4 wt % |

In the hydrogenated reaction mixture, the total amount of 1-MPE, 2-MPE, 1-MPV and 2-MPV as well as hydrocarboxylated compounds formed by hydrocarboxylating substituted propenyl groups of 1-MPE, 2-MPE, 1-MPV and 2-MPV was 1% by weight or less.

Preparation of α-(4-isobutylphenyl)propionic acid by hydrolysis of methyl α-(4-isobutylphenyl)propionate Experimental Example 36

Thirty grams of methyl α-(4-isobutylphenyl)propionate obtained by distilling the reaction mixture of Experimental Example 32 under reduced pressure and 150 ml of a 10% aqueous sodium hydroxide solution were refluxed with stirring in order to carry out hydrolysis for about 3 hours. After cooling, the mixture was allowed to stand, and a separated lower aqueous phase was then washed with normal hexane.

Afterward, 5% hydrochloric acid was added to the aqueous phase so as to adjust its pH to 2, and a separated oil portion was extracted with normal hexane and then washed with water. Normal hexane was vaporized out under reduced pressure in order to obtain 23.9 g of light yellow crude α-(4-isobutylphenyl)propionic acid crystals.

The crude α-(4-isobutylphenyl)propionic acid was recrystallized from a normal hexane solvent, thereby obtaining 20.7 g of white purified α-(4-isobutylphenyl)-propionic acid (melting point 75°–76° C.) crystals. Spectra of this product were in accord with those of a control.

Experimental Example 37

One hundred grams of the hydroesterified reaction mixture of Experimental Example 33 and 150 ml of a 10% aqueous sodium hydroxide solution were refluxed with stirring in order to carry out hydrolysis for about 3 hours. After cooling, the mixture was allowed to stand, and a separated lower aqueous phase was then washed with normal hexane.

Afterward, 5% hydrochloric acid was added to the aqueous phase so as to adjust its pH to 2, and a separated oil portion was extracted with normal hexane and then washed with water. Normal hexane was vaporized out under reduced pressure in order to obtain 22.4 g of light yellow crude α-(4-isobutylphenyl)propionic acid crystals.

The crude α-(4-isobutylphenyl)propionic acid was then recrystallized from a normal hexane solvent, thereby obtaining 19.9 g of white purified α-(4-isobutylphenyl)propionic acid (melting point 75°–76° C.) crystals. Spectra of this product were in accord with those of a control.

What is claimed is:

1. A method for preparing α-(4-isobutylphenyl)propionaldehyde which comprises the following steps (I), (II) and (III):

the step (I) of dehydrogenating p-isobutylethylbenzene in a gaseous phase in the presence of a dehydrogenating metal catalyst to form p-isobutylstyrene and at least one unsaturated hydrocarbon compound selected from the following group A;

the group A:
4-(2'-methyl-1'-propenyl)ethylbenzene,
4-(2'-methyl-1'-propenyl)vinylbenzene,
4-(2'-methyl-2'-propenyl)ethylbenzene, and
4-(2'-methyl-2'-propenyl)vinylbenzene;

the step (II) of reacting a mixture of p-isobutylstyrene obtained in said step (I) and at least one unsaturated hydrocarbon compound selected from said group A with carbon monoxide and hydrogen at a reaction temperature of 40° to 150° C. under a carbon monoxide/hydrogen mixed pressure of 10 to 600 kg/cm$^2$ in the presence of a transition metal complex carbonylating catalyst to form α-(4-isobutylphenyl)propionaldehyde and at least one unsaturated aldehyde selected from the following group B;

the group B:
α-[4-(2'-methyl-1'-propenyl)phenyl]propionaldehyde and
α-[4-(2'-methyl-2'-propenyl)phenyl]propionaldehyde; and the step III) of selectively hydrogenating at least one unsaturated aldehyde selected from said group B obtained in said step (II) only on the ethylenic carbon-carbon double bond thereof to prepare α-(4-isobutylphenyl)propionaldehyde.

2. A method for preparing α-(4-isobutylphenyl)propionaldehyde and 2-(4-isobutylphenyl)propanol which comprises the following steps (I), (II) and (III):

the step (I) of dehydrogenating p-isobutylethylbenzene in a gaseous phase in the presence of a dehydrogenating metal catalyst to form p-isobutylstyrene and at least one unsaturated hydrocarbon compound selected from the following group A;

the group A:
4-(2'-methyl-1'-propenyl)ethylbenzene,
4-(2'-methyl-1'-propenyl)vinylbenzene,
4-(2'-methyl-2'-propenyl)ethylbenzene, and
4-(2'-methyl-2'-propenyl)vinylbenzene;

the step (II) of reacting a mixture of p-isobutylstyrene obtained in said step (I) and at least one unsaturated hydrocarbon compound selected from said group A with carbon monoxide and hydrogen at a reaction temperature of 40° to 150° C. under a carbon monoxide/hydrogen mixed pressure of 10 to 600 kg/cm$^2$ in the presence of a transition metal complex carbonylating catalyst to form α-(4-isobutylphenyl)propionaldehyde and at least one unsaturated aldehyde selected from the following group B;

the group B:
α-[4-(2'-methyl-1'-propenyl)phenyl]propionaldehyde and
α-[4-(2'-methyl-2'-propenyl)phenyl]propionaldehyde; and the step (III) of hydrogenating at least one unsaturated aldehyde selected from said group B obtained in said step (II) to form 2-(4-isobutylphenyl)propanol.

3. A method for preparing α-(4-isobutylphenyl)propionaldehyde and 2-(4-isobutylphenyl)propanol which comprises the following steps (I), (II) and (III):

the step (I) of dehydrogenating p-isobutylethylbenzene in a gaseous phase in the presence of a dehydrogenating metal catalyst to form p-isobutylstyrene and at least one unsaturated hydrocarbon compound selected from the following group A;

the group A:
4-(2'-methyl-1'-propenyl)ethylbenzene,
4-(2'-methyl-1'-propenyl)vinylbenzene,
4-(2'-methyl-2'-propenyl)ethylbenzene, and
4-(2'-methyl-2'-propenyl)vinylbenzene;

the step (II) of reacting a mixture of p-isobutylstyrene obtained in said step (I) and at least one unsaturated hydrocarbon compound selected from said group A with carbon monoxide and hydrogen at a reaction temperature of 40° to 150° C. under a carbon monoxide/hydrogen mixed pressure of 10 to 600 kg/cm$^2$ in the presence of a transition metal complex carbonylating catalyst to form α-(4-isobutylphenyl)propionaldehyde and at least one unsaturated aldehyde selected from the following group B;

the group B:
α-[4-(2'-methyl-1'-propenyl)phenyl]propionaldehyde and
α-[4-(2'-methyl-2'-propenyl)phenyl]propionaldehyde; and the step (III) of hydrogenating one unsaturated aldehyde selected from said group B obtained in said step (II) to form α-(4-isobutylphenyl)propionaldehyde and 2-(4-isobutylphenyl)propanol.

4. A method for preparing α-(4-isobutylphenyl)propionaldehyde which comprises the following steps (I), (II) and (III):

the step (I) of dehydrogenating p-isobutylethylbenzene in a gaseous phase in the presence of a dehydrogenating metal catalyst to form p-isobutylstyrene and at least one unsaturated hydrocarbon compound selected from the following group A;

the group A:
4-(2'-methyl-1'-propenyl)ethylbenzene,
4-(2'-methyl-1'-propenyl)vinylbenzene,
4-(2'-methyl-2'-propenyl)ethylbenzene, and
4-(2'-methyl-2'-propenyl)vinylbenzene;

the step (II) of reacting a mixture of p-isobutylstyrene obtained in said step (I) and one unsaturated hydrocarbon compounds of said group A with carbon monoxide and hydrogen at a reaction temperature of 40° to 150° C. under a carbon monoxide/hydrogen mixed pressure of 10 to 600 kg/cm$^2$ in the presence of a transition metal complex carbonylating catalyst to form α-(4-isobutylphenyl)propionaldehyde and at least one unsaturated aldehyde selected from the following group B;

the group B:
α-[4-(2'-methyl-1'-propenyl)phenyl]propionaldehyde and
α-[4-(2'-methyl-2'-propenyl)phenyl]propionaldehyde; and the step (III) of hydrogenating at least one unsaturated compound selected from the following group C consisting of unreacted unsaturated hydrocarbon compounds in said step (II) to form p-isobutylethylbenzene, and recycling at least a part of the latter through said dehydrogenation step (I) as the raw material of said dehydrogenation step (I);

the group C:
4-(2'-methyl-1'-propenyl)ethylbenzene and
4-(2'-methyl-2'-propenyl)ethylbenzene.

5. A method for preparing α-(4-isobutylphenyl)propionic acid or its alkyl ester which comprises the following steps (I), (II) and (III):

the step (I) of dehydrogenating p-isobutylethylbenzene in a gaseous phase in the presence of a dehydrogenating metal catalyst to form p-isobutylstyrene and at least one unsaturated hydrocarbon compound selected from the following group A;

the group A:
4-(2'-methyl-1'-propenyl)ethylbenzene,
4-(2'-methyl-1'-propenyl)vinylbenzene,
4-(2'-methyl-2'-propenyl)ethylbenzene, and
4-(2'-methyl-2'-propenyl)vinylbenzene;

the step (II) of reacting a mixture of p-isobutylstyrene obtained in said step (I) and at least one unsaturated hydrocarbon compound selected from said group A with carbon monoxide and water or a lower alcohol at a reaction temperature of 40° to 250° C. under a pressure of 10 to 600 kg/cm$^2$ in the presence of a transition metal complex carbonylating catalyst to form α-(4-isobutylphenyl)propionic acid or its alkyl ester and at least one unsaturated acid or its ester selected from the following group B;

the group B:
α-[4-(2'-methyl-1'-propenyl)phenyl]propionic acid or its alkyl ester and
α-[4-(2'-methyl-2'-propenyl)phenyl]propionic acid or its alkyl eser; and the step (III) of hydrogenating at least one unsaturated acid or its ester selected from said group B obtained in said step (II) to form α-(4-isobutylphenyl)propionic acid or its alkyl ester.

6. A method for preparing α-(4-isobutylphenyl)propionic acid or its alkyl ester which comprises the following steps (I), (II) and (III):

the step (I) of dehydrogenating p-isobutylethylbenzene in a gaseous phase in the presence of a dehydrogenating metal catalyst to form p-isobutylstyrene and at least one unsaturated hydrocarbon compound selected from the following group A;

the group A:
4-(2'-methyl-1'-propenyl)ethylbenzene,
4-(2'-methyl-1'-propenyl)vinylbenzene,
4-(2'-methyl-2'-propenyl)ethylbenzene, and
4-(2'-methyl-2'-propenyl)vinylbenzene;

the step (II) of reacting a mixture of p-isobutylstyrene obtained in said step (I) and at least one unsaturated hydrocarbon compound selected from said group A with carbon monoxide and water or a lower alcohol at a reaction temperature of 40° to 250° C. under a pressure of 10 to 600 kg/cm$^2$ in the presence of a transition metal complex carbonylating catalyst to form α-(4-isobutylphenyl)propionic acid or its alkyl ester and at least one unsaturated acid or its ester selected from the following group B;

the group B:
α-[4-(2'-methyl-1'-propenyl)phenyl]propionic acid or its alkyl ester and
α-[4-(2'-methyl-2'-propenyl)phenyl]propionic acid or its alkyl eser; and the step (III) of hydrogenating at least one unsaturated compound selected from the following group C consisting of unreacted unsaturated hydrocarbon compounds in said step (II) to form p-isobutylethylbenzene, and recycling at least a part of the latter through said dehydrogenation step (I) as the raw material in said dehydrogenation step (I);

the group C:
4-(2'-methyl-1'-propenyl)ethylbenzene and
4-(2'-methyl-2'-propenyl)ethylbenzene.

7. A method as in one of claims 1 to 6 wherein said dehydrogenating metal catalyst in said step (I) contains a metal selected from the group consisting of metals in the groups Ib, IIb, VIa, VIIa and VIII of the periodic table.

8. A method as in one of claims 1 to 6 further containing the step of oxidizing obtained α-(4-isobutylphenyl)-propanol to form α-(4-isobutylphenyl)propionic acid.

9. A method as in one of claims 1 to 6 further containing the step of hydrolyzing obtained alkyl α-(4-isobutylphenyl)propionate to form α-(4-isobutylphenyl)propionic acid.

10. A method as in one of claims 1 to 6 wherein said step (I) is the following step (I):

the step (I) of dehydrogenating p-isobutylethylbenzene in a gaseous phase in the presence of a dehydrogenating metal catalyst containing a metal selected from the group consisting of metals in the groups Ib, IIb, VIa, VIIa and VIII of the periodic table under conditions of a reaction temperature of 300° to 650° C., a reaction pressure of 50 kg/cm² or less, a contact time of 0.005 to 20 seconds and a p-isobutylethylbenzene conversion of 80% by weight or less, in order to form p-isobutylstyrene and at least one unsaturated hydrocarbon compound selected from the following group A;

the group A:
4-(2'-methyl-1'-propenyl)ethylbenzene,
4-(2'-methyl-1'-propenyl)vinylbenzene,
4-(2'-methyl-2'-propenyl)ethylbenzene and
4-(2'-methyl-2'-propenyl)vinylbenzene.

11. A method according to claim 10 wherein said dehydrogenating metal catalyst contains a metal selected from the group consisting of iron, copper, zinc, nickel, palladium, platinum, cobalt, rhodium, iridium, ruthenium, chromium and molybdenum.

12. A method as in one of claims 1 to 6 wherein said hydrogenation is achieved by using hydrogen in the presence of a hydrogenating metal catalyst.

13. A method as in one of claims 1-12 wherein said hydrogenation is achieved by using hydrogen at a reaction temperature ranging from ordinary temperature to 300° C. under a hydrogen pressure of from atmospheric pressure to 300 kg/cm² in the presence of a hydrogenating metal catalyst.

14. A method according to claim 12 or 13 wherein said metal in said hydrogenating metal catalyst is at least one metal selected from the group consisting of Fe, Co, Ni, Ru, Rh, Pd, Os, Ir, Pt, Cu, Re, Mo, W, Cr and Ta.

15. A method for preparing α-(4-isobutylphenyl)propionic acid or its precursor which comprises the following steps (1) and (2):

the step (1) of dehydrogenating p-isobutylethylbenzene in a gaseous phase in the presence of a dehydrogenating metal catalyst to obtain a mixture of p-isobutylstyrene and at least one unsaturated hydrocarbon compound selected from the group consisting of 4-(2'-methyl-1'-propenyl)ethylbenzene and 4-(2'-methyl-2'-propenyl)ethylbenzene; and the step (2) of reacting a mixture of p-isobutylstyrene and at least one unsaturated hydrocarbon compound selected from the group consisting of 4-(2'-methyl-1'-propenyl)ethylbenzene and 4-(2'-methyl-2'-propenyl)ethylbenzene, with carbon monoxide and water or a lower alcohol in the presence of a transition metal complex carbonylating catalyst at a reaction temperature of 40° to 250° C. under a pressure of 10 to 600 kg/cm² to form α-(4-isobutylphenyl)propionic acid or an alkyl α-(4-isobutylphenyl)propionate selectively.

16. A method for preparing α-(4-isobutylphenyl)propionic acid or its precursor which comprises the following steps (1), (2), (3) and (4):

the step (1) of dehydrogenating p-isobutylethylbenzene in a gaseous phase in the presence of a dehydrogenating metal catalyst to obtain a mixture of p-isobutylstyrene and at least one unsaturated hydrocarbon compound selected from the group consisting of 4-(2'-methyl-1'-propenyl)ethylbenzene and 4-(2'-methyl-2'-propenyl)ethylbenzene;

the step (2) of reacting a mixture of p-isobutylstyrene and at least one unsaturated hydrocarbon compound selected from the group consisting of 4-(2'-methyl-1'-propenyl)ethylbenzene and 4-(2'-methyl-2'-propenyl)ethylbenzene, with carbon monoxide and water or a lower alcohol in the presence of a transition metal complex carbonylating catalyst at a reaction temperature of 40° to 250° C. under a pressure of 10 to 600 kg/cm² to form α-(4-isobutylphenyl)propionic acid or an alkyl α-(4-isobutylphenyl)propionate selectively;

the step (3) of recovering said unsaturated hydrocarbon compound from the reacted mixture in said step (2); and the step (4) of hydrogenating said recovered unsaturated hydrocarbon compound of step (3) to obtain p-isobutylethylbenzene, and recycling at least a part of the latter through said dehydrogenation step (1) as the raw material of said dehydrogenation step (1).

17. A method for preparing α-(4-isobutylphenyl)propionaldehyde or its precursor which comprises the following steps (1) and (2):

the step (1) of dehydrogenating p-isobutylethylbenzene in a gaseous phase in the presence of a dehydrogenating metal catalyst to obtain a mixture of p-isobutylstyrene and at least one unsaturated hydrocarbon compound selected from the group consisting of 4-(2'-methyl-1'-propenyl)ethylbenzene and 4-(2'-methyl-2'-propenyl)ethylbenzene; and the step (2) of reacting a mixture of p-isobutylstyrene and at least one unsaturated hydrocarbon compound selected from the group consisting of 4-(2'-methyl-1'-propenyl)ethylbenzene and 4-(2'-methyl-2'-propenyl)ethylbenzene, with carbon monoxide and hydrogen in the presence of a transition metal complex carbonylating catalyst at a reaction temperature of 40° to 150° C. under a carbon monoxide/hydrogen mixed pressure of 10 to 600 kg/cm$^2$ to form α-(4-isobutylphenyl)propionaldehyde selectively.

18. A method for preparing α-(4-isobutylphenyl)propionaldehyde or its precursor which comprises the following steps (1), (2), (3) and (4):

the step (1) of dehydrogenating p-isobutylethylbenzene in a gaseous phase in the presence of a dehydrogenating metal catalyst to obtain a mixture of p-isobutylstyrene and at least one unsaturated hydrocarbon compound selected from the group consisting of 4-(2'-methyl-1'-propenyl)ethylbenzene and 4-(2'-methyl-2'-propenyl)ethylbenzene;

the step (2) of reacting a mixture of p-isobutylstyrene and at least one unsaturated hydrocarbon compound selected from the group consisting of 4-(2'-methyl-1'-propenyl)ethylbenzene and 4-(2'-methyl-2'-propenyl)ethylbenzene, with carbon monoxide and hydrogen in the presence of a transition metal complex carbonylating catalyst at a reaction temperature of 40° to 150° C. under a carbon monoxide/hydrogen mixed pressure of 10 to 600 kg/cm$^2$ to form α-(4-isobutylphenyl)propionaldehyde selectively;

the step (3) of recovering said unsaturated hydrocarbon compound from the reacted mixture in said step (2); and the step (4) of hydrogenating said recovered unsaturated hydrocarbon compound of step (3) to obtain p-isobutylethylbenzene, and recycling at least a part of the latter through said dehydrogenation step (19 as the raw material of said dehydrogenation step (1).

19. A method for preparing α-(4-isobutylphenyl)propionic acid or its precursor which comprises the following steps (1) and (2):

the step (1) of dehydrogenating p-isobutylethylbenzene in a gaseous phase in the presence of a dehydrogenating metal catalyst to obtain a mixture of p-isobutylstyrene and at least one unsaturated hydrocarbon compound selected from the group consisting of 4-(2'-methyl-1'-propenyl)vinylbenzene and 4-(2'-methyl-2'-propenyl)vinylbenzene; and the step (2) of reacting a mixture of p-isobutylstyrene and at least one unsaturated hydrocarbon compound selected from the group consisting of 4-(2'-methyl-1'-propenyl)vinylbenzene and 4-(2'-methyl-2'-propenyl)vinylbenzene, with carbon monoxide and water or a lower alcohol in the presence of a transition metal complex carbonylating catalyst at a reaction temperature of 40° to 250° C. under a pressure of 10 to 600 kg/cm$^2$ to form α-(4-isobutylphenyl)propionic acid or an alkyl α-(4-isobutylphenyl)propionate and at least one unsaturated acid or its ester selected from the group consisting of α-[4-(2'-methyl-1'-propenyl)phenyl]propionic acid or its alkyl ester and α-[4-(2'-methyl-2'-propenyl)phenyl]propionic acid or its alkyl ester.

20. A method for preparing α-(4-isobutylphenyl)propionic acid or its precursor which comprises the following steps (1), (2) and (3):

the step (1) of dehydrogenating p-isobutylethylbenzene in a gaseous phase in the presence of a dehydrogenating metal catalyst to obtain a mixture of p-isobutylstyrene and at least one unsaturated hydrocarbon compound selected from the group consisting of 4-(2'-methyl-1'-propenyl)vinylbenzene and 4-(2'-methyl-2'-propenyl)vinylbenzene;

the step (2) of reacting a mixture of p-isobutylstyrene and at least one unsaturated hydrocarbon compound selected from the group consisting of 4-(2'-methyl-1'-propenyl)vinylbenzene and 4-(2'-methyl-2'-propenyl)vinylbenzene, with carbon monoxide and water or a lower alcohol in the presence of a transition metal complex carbonylating catalyst at a reaction temperature of 40° to 250° C. under a pressure of 10 to 600 kg/cm$^2$ to form α-(4-isobutylphenyl)propionic acid or an alkyl α-(4-isobutylphenyl)propionate and at least one unsaturated acid or its ester selected from the group consisting of α-[4-(2'-methyl-1'-propenyl)phenyl]propionic acid or its alkyl ester and α-[4-(2'-methyl-2'-propenyl)phenyl] propionic acid or its alkyl ester; and the step (3) of hydrogenating said unsaturated acid or its alkyl ester in said step (2) to form α-(4-isobutylphenyl)propionic acid or its alkyl ester.

21. A method for preparing α-(4-isobutylphenyl)propionaldehyde or its precursor which comprises the following steps (1) and (2):

the step (1) of dehydrogenating p-isobutylethylbenzene in a gaseous phase in the presence of a dehydrogenating metal catalyst to obtain a mixture of p-isobutylstyrene and at least one unsaturated hydrocarbon compound selected from the group consisting of 4-(2'-methyl-1'-propenyl)vinylbenzene and 4-(2'-methyl-2'-propenyl)vinylbenzene; and the step (2) of reacting a mixture of p-isobutylstyrene and at least one unsaturated hydrocarbon compound selected from the group consisting of 4-(2'-methyl-1'-propenyl)vinylbenzene and 4-(2'-methyl-2'-propenyl)vinylbenzene, with carbon monoxide and hydrogen in the presence of a transition metal complex carbonylating catalyst at a reaction temperature of 40° to 150° C. under a carbon monoxide/hydrogen mixed pressure of 10 to 600 kg/cm$^2$ to form α-(4-isobutylphenyl)propionaldehyde and at least one unsaturated aldehyde selected from the group consisting of α-[4-(2'-methyl-1'-propenyl)phenyl]propionaldehyde and α-[4-(2'-methyl-2'-propenyl)phenyl] propionaldehyde.

22. A method for preparing α-(4-isobutylphenyl)propionaldehyde or its precursor which comprises the following steps (1), (2) and (3):

the step (1) of dehydrogenating p-isobutylethylbenzene in a gaseous phase in the presence of a dehydrogenating metal catalyst to obtain a mixture of p-isobutylstyrene and at least one unsaturated hydrocarbon compound selected from the group consisting of 4-(2'-methyl-1'-propenyl)vinylbenzene and 4-(2'-methyl-2'-propenyl)vinylbenzene;

the step (2) of reacting a mixture of p-isobutylstyrene and at least one unsaturated hydrocarbon compound selected from the group consisting of 4-(2'-methyl-1'-propenyl)vinylbenzene and 4-(2'-methyl-2'-propenyl)vinylbenzene, with carbon monoxide and hydrogen in the presence of a transition metal complex carbonylating catalyst at a reaction temperature of 40° to 150° C. under a carbon monoxide/hydrogen mixed pressure of 10 to 600 kg/cm$^2$ to form α-(4-isobutylphenyl)propionaldehyde and at least one unsaturated aldehyde selected from the group consisting of α-[4-(2'-methyl-1'-propenyl)- phenyl]propionaldehyde and α-[4-(2'-methyl-2'-propenyl)phenyl]propionaldehyde; and the step (3) of hydrogenating said unsaturated aldehyde in said step (2) to form 2-(4-isobutylphenyl)-propanal or α-(4-isobutylphenyl)propionaldehyde.

23. The method according to claims 15, 16, 19 or 20, wherein said transition metal complex carbonylation catalyst contains a transition metal selected from the group consisting of palladium, rhodium and iridium.

24. The method according to claims 17, 18, 21 or 22 wherein the transition metal complex carbonylation catalyst contains a transition metal selected from the group consisting of palladium, rhodium, iridium and ruthenium.

25. The method according to claim 13 wherein the metal in the hydrogenation metal catalyst is at least one metal selected from the group consisting of Fe, Co, Ni, Ru, Rh, Pd, Os, Fr, Pt, Cu, Re, Mo, W, Cr, and Ta.

* * * * *

UNITED STATES PATENT AND TRADEMARK OFFICE
CERTIFICATE OF CORRECTION

PATENT NO. : 5,260,477
DATED : November 9, 1993
INVENTOR(S) : Isoo Shimizu, et al.

It is certified that error appears in the above-indentified patent and that said Letters Patent is hereby corrected as shown below:

Column 1, line 41: "(4- ) isobutylphenyl" should read --(4-isobutylphenyl--

Column 3, line 6: "present" should read --presence--

Column 4, line 29: delete second occurrence of "of"

Column 7, line 6: "byproduct" should read --by product--

Column 8, line 60: after "propenyl" insert --)--

Column 9, line 24: "group." should read --group,--

Column 9, lines 53 & 54: "triphenylphophine, tritolylphophine" should read --triphenlylphosphine, tritolylphosphine--

Column 10, line 28: "kg/cm$^2$," should read --kg/cm$^2$,--

Column 10, line 33: after "the" delete --25--

Column 11, line 18: delete "and"

Column 11, line 19: after "propionaldehyde" insert --and--

Column 8, line 60, "benzene" should read --ethylbenzene--.

UNITED STATES PATENT AND TRADEMARK OFFICE
CERTIFICATE OF CORRECTION

PATENT NO. : 5,260,477

DATED : November 9, 1993

INVENTOR(S) : Isoo Shimizu, et al.

Page 2 of 3

It is certified that error appears in the above-indentified patent and that said Letters Patent is hereby corrected as shown below:

Column 11, lines 55-56: delete "phenyl)propionaldehyde which is the desired compound of"

Column 13, lines 34-35: "pronionic" should read --propionic--

Column 14, line 67: "kg/cm$^{2}$'" should read --kg/cm$^2$,--

Column 23, line 56: "obtain" should read --obtained crude--

Column 24, line 15: "26.2 g of light yellow crude" should read --26.8 g of light yellow crude -(4-isobutylphenyl)propionic acid crystals.--

Column 24, line 37: "butyenylstyrene" should read --butenylstyrene--

Column 25, line 27: "8%." should read --8%--

Column 28, line 42, Claim 1: "III)" should read --(III)--

Column 30, line 44, Claim 5: "eser" should read --ester--

Column 31, line 8, Claim 6: "eser" should read --ester--

UNITED STATES PATENT AND TRADEMARK OFFICE
CERTIFICATE OF CORRECTION

PATENT NO. : 5,260,477
DATED : November 9, 1993
INVENTOR(S) : Isoo Shimizu, et al.

It is certified that error appears in the above-indentified patent and that said Letters Patent is hereby corrected as shown below:

Column 31, line 26, Claim 8: "propanol" should read --propionaldehyde or 2-(4-isobutylphenyl)propanol--

Column 33, line 34, Claim 18: "(19" should read --(1)--

Column 35, line 6, Claim 22: "propanal" should read --propanol--

Signed and Sealed this

Eighteenth Day of October, 1994

Attest:

BRUCE LEHMAN

Attesting Officer

Commissioner of Patents and Trademarks